US007067248B2

(12) United States Patent
Hruby et al.

(10) Patent No.: US 7,067,248 B2
(45) Date of Patent: Jun. 27, 2006

(54) SCREENING METHOD FOR ORTHOPOXVIRUS ANTIVIRALS

(75) Invent

Amino acid sequence

```
              P20      P15      P10      P5    P1   P1*   P5*      P10*     P15*     P20*
VV/P25K  --DTIFFAGSISEYDDLQMMIAG  *  AKSKFPRSMLSIFNIVPRTMS--
FP/FP5   --GEKALCAQVTRDQLLEIIAAG  *  ARSKFPKSLLSMYRVTPRVMT--
VV/P4b   --LSCSVCNSLSQIVDDDFISAG  *  ARNQRTKPKRAGNNQSQQPIK--
FP/FP4b  --NLCNVCDVLNKITEEDVISAG  *  AKQQRPMRLRSKPKPDICKGV--
VV/P17K  --GDAAVKGGNNNLNSQTDVTAG  *  ACDTKSKSSKCITCKPKSKSS--
VV/P21K       MSYLRRYYNMLDDESAG  *  AGVLDKDLFTEEQQQSFMPKD--

VV/P4a   --GEDIFCAMPYNILDRIITNAG  *  TCTVSIGDMLDNITTQSDCNM--
VV/P4a   --FRDYQSYRQYRNYCPRYFYAG  *  SPEGEETIICDSEPISILDRI--
```

FIG. 5

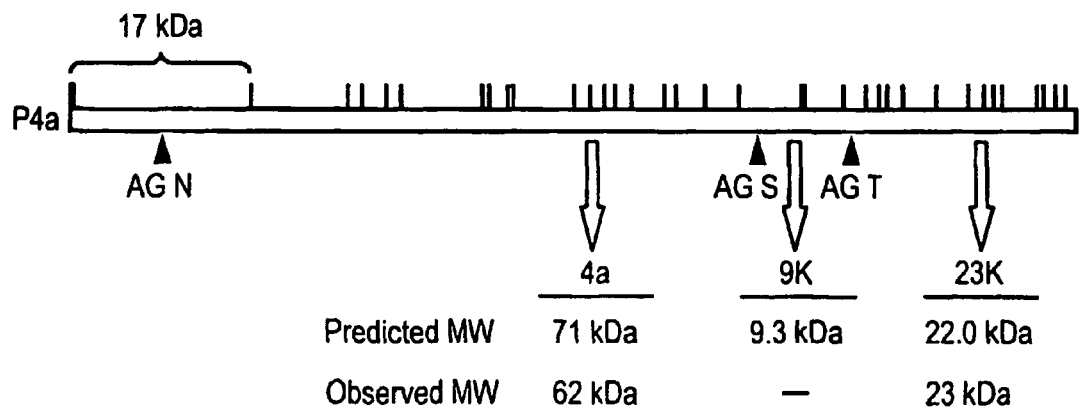

FIG. 6

| ORF | Protein | Temporal class | Locale[a] | Cleaved |
|---|---|---|---|---|
| A10L | P4a | Late | Core | + |
| L4R | P25K | Late | Core | + |
| A3L | P4b | Late | Core | + |
| A12L | P17K | Late | Core | + |
| A17L | P21K | Late | Virion | + |
| F13L | P37K | Late | Envelope | − |
| E9L | DNAP | Early | Virosome | − |
| K1L | HR | Imm. Early[b] | Nonstructural[c] | − |

FIG. 7

| Enzyme | Sequence[a] |
|---|---|
| G11[b] | GIA H̲LLE̲H LLI-64-E̲NE̲ |
| | |
| Protease III | GLA HYLEH MLF-38-END |
| dIDE | GLA HFCEH MLF-8-ENG |
| hIDE | GLS HFCEH MLF-8-ENE |
| | |
| Thermolysin | VVA HELTH AVT-14-INE |
| Aminopeptidase N | VIA HELAH QWF-13-LNE |
| Collagenase[c] | VAA HELGH SLG |

Hydrophobicity Profile of Vaccina virus I7L protein

Variola virus K7L
Camelpox virus
Monkeypox virus I7L

Homology to ASFV

I7L  423 amino acids 344 ts16 mutation P→L

| | | |
|---|---|---|
| VV I7L 241/ HWKCVIYDK--KQCLVSFYDSGGN /262 | 314/ GCINVEVNQ--LLESECGMFISLF /335 |
| ASFV 168/ HWVAIFVDMRGDCWSIEYFNSAGN /291 | 218/ LAVTNIRHQ-RSQTECGPYSLFY /239 |
| ADE2 54/ HWMAFAWNP--RSKTCYLFEPFGF /75 | 107/ LEKSTQSVQGPNSAACGLFCCMF /129 |
| U1p1 514/ HWALGIIDL--KKKTIGYVDSLSN /35 | 566/ LIHLDCPQQ--PNGYDCGIYVCMN /587 |

| Cotransfection plasmid | P4a(A10L) | P4b(A3L) | P25K(L4R) |
|---|---|---|---|
| pI7L | + | + | + |
| pH241A | - | - | - |
| pW242A | - | - | - |
| pD248A | - | - | - |
| pD258A | - | + | + |
| pQ322A | - | - | - |
| pC328A | - | - | - |
| pG329A | - | - | - |

FIG. 20

| Plasmids used to rescue ts16 | Fold Rescue |
|---|---|
| Ts16 VV alone | 1 |
| pI7L | 7 |
| pI7L-T | 1 |
| pH241A | 1 |
| pW242A | 1 |
| pD248A | 2 |
| pD258A | 3 |
| pQ322A | 1 |
| pC328A | 1 |
| pG329A | 1 |

FIG. 21

SCREENING METHOD FOR ORTHOPOXVIRUS ANTIVIRALS

This is a U.S. National Stage application of PCT/US03/00347, filed 8 Jan. 2003, which claims benefit of provisional application No. 60/345,646, filed 8 Jan. 2002.

FEDERAL GOVERNMENT SUPPORT

The present invention was developed in part with funding from the United States Government, NIH Grant number AI-48486-02.

BACKGROUND OF THE INVENTION

1. Field of the Invention

The focus of the present invention is an effective anti-poxvirus drug for use in treating or preventing human disease caused by pathogenic poxviruses. More particularly, the present invention relates to antiviral drugs that target the poxvirus proteinase responsible for core protein maturation, a step which is absolutely essential for the production and spread of infectious virions.

2. Description of the Related Art

The specter of bioterrorism has cast a pall over modern society. The ability to grow and manipulate microorganisms has provided biomedical scientists with a marvelous set of new abilities to develop therapies and drugs to combat both infectious and genetic diseases. Unfortunately these same technologies have a dark side. With very little sophisticated equipment required, the tools of microbiology and genetic engineering allow individuals or organizations to readily prepare large quantities of pathogenic microorganisms for deliberate dispersal into the environment. Unlike conventional weapons, pathogenic microorganisms have the ability to replicate and spread, they do not distinguish between the soldier and the civilian, and once released, they can not be recalled or controlled.

Whereas biological warfare concerns were originally limited to their potential deployment during conflicts between the armed forces of industrialized nations, the escalating threat of terrorism and domestic violence now raises the possibility that these agents may be used for this purpose as well. Amongst the biological agents that are believed to pose the greatest threat in this regard are *Bacillus anthracis* (anthrax), *Yersinia pestis* (bubonic plague), *Francisella tularensis* (tularemia), *Coxiella burnetti* (Q fever), hemorrhagic RNA viruses (e.g., Dengue, Marburg, Ebola, and Venezuelan Equine Encephalitis), and smallpox. While deliberate introduction of any of these agents would be devastating, the one which holds the greatest potential for harming the general population is smallpox, or a related genetically-engineered orthopoxvirus.

Smallpox was the most destructive disease in recorded history. It is estimated to have killed, crippled or disfigured nearly 1/10 of all humankind. In the 20$^{th}$ century alone, more than 300 million people succumbed to the disease. Variola virus, the causative agent of smallpox, is extremely infectious, causing obvious disease in most susceptible individuals that it comes into contact with.

Smallpox is usually contracted by inhalation of aerosol droplets spread by infected individuals. Following a 10–14 day prodrome period, frank disease erupts which is characterized by high fever and malaise. Two to three days later the patient's temperature drops and a systemic rash appears, characterized by the prototypic pustular lesions which can last 2–3 weeks. With the more virulent forms of smallpox, such as that caused by Variola major, as many as 30% of infected individuals die. Those that recover are scarred for life.

The disease has a number of features that make it "ideal" as an agent of bioterrorism: 1) the virus is easy to grow, can be lyophilized and does not require a cold chain to maintain viability; 2) the infection is spread by the respiratory route; 3) the prolonged prodrome period, combined with the ease of modern travel, allows the infected individual to spread the disease widely; 4) the resultant scarring has lasting psychological consequences; and 5) the virus is very stable in the environment after it has been shed, making decontamination difficult.

Although smallpox is of paramount concern, other potential orthopoxvirus pathogens should not be neglected. For example, there have been several recent incursions of monkeypox virus into the human population, although the human-human spread seems limited thus far. Another, more chilling, scenario is the possibility that a laboratory strain of vaccinia virus or cowpox virus could be genetically engineered to produce a toxin to convert it into a potent pathogen. Fortunately, the orthopoxviruses are highly related at the DNA level (e.g. 90% between variola and vaccinia) making it likely that any antiviral agent developed would inhibit the replication of this entire group of viruses.

Smallpox is no longer present in the natural environment, with the few known remaining laboratory stocks of variola virus slated for destruction in the near future. The eradication of smallpox was possible because it is a human-specific disease with no animal reservoirs, there was a single serotype, and the attenuated vaccine developed by Jenner effectively stimulates both the cellular and humoral arms of the immune system, providing long-lasting immunity. Smallpox was eliminated from the U.S. in the 1960's, and routine prophylactic immunization was discontinued in 1973.

The subsequent 30 years have produced a population that is immunologically naive and highly susceptible to orthopoxvirus infection. Due to the small but significant risk of serious complications from vaccination, especially in those immunocompromised due to infection by HIV or other agents, mass immunization of the populace is not advisable. Nevertheless, in the event that an infectious orthopoxvirus were introduced into the population, the live vaccine would be an effective weapon in limiting the spread of the disease once it had been diagnosed.

Vaccination before exposure, or within 2–3 days after exposure, affords almost complete protection. Vaccination as late as 4–5 days post-exposure can protect against death. Unfortunately, in the event of a deliberate introduction of the infectious agent into a heavily populated area, there would be a large reservoir of infected individuals by the time the sentinel cases were diagnosed. Furthermore, relatively limited stocks of the vaccine are available. For these reasons, as a protective measure, it is imperative that an effective anti-orthopoxvirus drug be available to treat those individuals exposed to the virus who have insufficient time to produce protective immunity and to help stem an epidemic.

The only well-known drug which is effective at inhibiting orthopoxvirus infections in cultured cells is methisazone or IBT (N-methylisatin β-thiosemicarbazone). However, this drug is of limited value in treating infected humans. Cidofovir has been demonstrated to be a potent anti-orthopoxvirus inhibitor, but it has severe side effects and must be delivered by injection. Thus, no safe, effective, orally-administrable anti-orthopoxvirus drug is currently available.

General Overview of Viral Proteolysis.

The term "limited proteolysis" was first introduced by Linderstrom-Lang and Ottesen to describe reactions in which the peptide bonds in a polypeptide are selectively hydrolyzed, as opposed to protein degradation which involved extensive cleavage of the peptide bonds in the substrate. The enzymes required for the peptide bond cleavage are named proteases which are divided into peptidases and proteinases. Peptidases are exopeptidases which hydrolyze single amino acids from the amino-terminus or the carboxy-terminus of a peptide chain. In contrast, the proteinases (also called proteolytic enzymes or endopeptidases) are capable of selectively recognizing and cleaving specific peptide bonds in substrates.

Proteinases are further subdivided into four classes based on the identity of their catalytic amino acid residues, whose relative three-dimensional positions are conserved within a group, and the mechanism of catalysis. The four types of proteinases are: serine, cysteine (thiol), aspartic (acid) and metallo-. Serine proteinases possess a catalytic triad of aspartic acid, histidine and serine residues, and appear to be the most common and widespread type of proteinase. Cysteine proteinases maintain a catalytic diad composed of cysteine and histidine residues in close proximity, whereas the catalytic diad of aspartic proteinases requires two aspartic acid residues. For the metalloproteinases, a divalent cation (usually $Zn^{+2}$) is required together with essential histidine and glutamic acid residues for catalysis.

Proteinases can be thought of in their most basic form as having a catalytic site, as described above, and a substrate binding pocket. The two sites are usually in close proximity. Generally, proteinases are composed of two globular domains, with amino acids involved in catalysis being contributed by each half of the substrate-binding crevice. For most serine, cysteine and aspartic proteinases, the two globular domains are found within the same polypeptide. However, in the case of the retroviral proteinases, a dimer complex is employed to bring together two individual catalytic centers to form the crevice. Although nearly all substrate-binding crevices achieve a similar three-dimensional structure with respect to the catalytic amino acids for each class of proteinase, the structural conservation does not extend to the substrate binding pocket, which distinguishes a given proteinase from all others. It is this substrate binding region which confers specificity to the proteinase.

It is generally accepted that for the hydrolysis of a specific peptide bond to occur, two requirements must be met. First, the susceptible peptide bonds need to be defined by the nearby amino acid residues with specific side chains which are required for the primary and secondary specificity. The primary specificity has a qualitative feature which targets the selection of the scissile bond, and the secondary specificity conveys a quantitative feature by facilitating the cleavage of the selected bond. Second, the susceptible bond is usually displayed adjacent to the surface of the substrate in a flexible region accessible to the proteinase, and the susceptible peptide must be presented in a three-dimensional conformation which fits the active site pocket of the proteinase. This is referred to as "conformational specificity".

Many types of post-translational modifications such as phosphorylation, glycosylation and acylation are required for the acquisition and regulation of protein properties such as enzyme activity, protein-protein interactions and intracellular localization. Likewise, limited proteolysis is often used to regulate protein activation or assembly by causing changes in the tertiary structure which bring distant functional amino acid residues together. Interestingly, the free energy required for the reconstruction of the hydrolyzed peptide bond is high and no biological mechanisms for repairing the broken peptide bond have yet been identified. Thus the changes introduced into substrates by proteolytic cleavage are essentially irreversible. This combination of cleavage specificity and reaction irreversibility have resulted in the common utilization of the proteolytic processing reaction as a unidirectional mechanism for a wide variety of biological processes including food digestion, signal peptide cleavage, signal transduction, peptide hormone/growth factor production, blood clotting, complement pathway cascade, pathogen elimination, cell migration and reproduction.

For many plant and animal viruses, a successful infection is dependent on proteolytic processing at one or more stages. In fact, it is the exceptional virus that does not require proteolytic processing during its replication cycle. The required proteolytic enzymes can be provided by either the host cell, the infecting virus, or both. Proteinases provided by the host cell generally contribute to the processing of membrane or envelope proteins that are trafficking through the secretory compartment of the cell. It is within these secretory compartments that viral envelope proteins undergo maturation by cleavage of signal peptides (in addition to acylation and glycosylation), such as the E1 and E2 glycoproteins of Sindbis virus. On the other hand, the proteinases which are responsible for the proteolytic processing of viral proteins are usually encoded by the viruses themselves.

Proteolytic cleavage of viral polypeptides has been categorized as "formative" or "morphogenic" proteolysis, depending on the function the reaction serves during the replicative cycle. Formative proteolysis refers to the processing of viral polyproteins into structural and non-structural protein products. A number of viral formative cleavage proteinases have been identified and are encoded by animal viruses such as picomaviruses, flaviviruses, alphaviruses, retroviruses and coronaviruses. Formative proteolysis provides a mechanism for viruses, such as retroviruses and positive-strand RNA viruses, to utilize a single RNA template for the expression of several viral proteins from a large polyprotein precursor. Morphogenic proteolysis refers to the cleavage of viral structural proteins assembled in previrions during virion maturation. Morphogenic cleavage occurs in conjunction with virion assembly and is often required for the acquisition of infectivity of both DNA and RNA viruses such as picomaviruses, alphaviruses, retroviruses, adenoviruses and bacteriophage T4. Although less is known about morphogenic proteolysis, several different functions have been proposed for this process, including: facilitation of correct genomic RNA dimerization in assembling retroviral particles; unidirectional packaging of bacteriophage T4 DNA; completion of the infectious poliovirus virion in a flexible configuration; and promotion of proper disassembly of adenovirus particles during the initiation of infection.

Regardless of the type of proteolytic maturation reaction employed, it is essential that the activity of the viral proteinases be properly regulated to ensure the efficient production of infectious progeny virions. In general, within biological systems, regulation of proteinases is achieved in several ways, including differential compartmentalization of the enzymes and substrate, presence of specific inhibitors and/or activators, and the proteolytic activation of zymogens. Viruses have adopted similar strategies. For example, in the retroviruses the acidic extracellular environment has been proposed to trigger the morphogenic cleavage of structural proteins by displacing a portion of the gag-pol polyprotein which prevents the active site of the proteinase from interacting with its substrate while within the cell. In the case of adenoviruses, it appears that DNA and a disulfide-linked peptide produced from the pVI structural protein during the latter stages of replication are required for the activation of the viral proteinase and subsequent virus maturation. Finally, perhaps the most elegant example of regulating viral proteinase activity is provided by the core protein of Sindbis virus which undergoes autoproteolysis to become inactive after assembly of the nucleocapsid. Inactivation of the proteinase activity is accomplished by locating the carboxy-terminal region of the protein into the catalytic pocket in concert with the proteolytic cleavage event.

VV Replication Cycle and Postranslational Modification of Viral Gene Products.

Given the importance of limited proteolysis as a means to regulate gene expression in biological systems, and the extent and diversity of ways that even simple viral systems apparently employ this regulatory mechanism, it is of interest to consider if and how a complex virus such as vaccinia virus might incorporate this process into its replicative cycle. Vaccinia virus (VV) is the prototype of the Poxviridae, a family of DNA viruses distinguished by their unique morphology and cytoplasmic site of replication.

The 191 Kbp VV DNA genome encodes at least 263 gene products whose expression is regulated in a temporal fashion during the viral replicative cycle that begins with entry of the virus into the host cell and terminates with the assembly of complex macromolecular structures to form an infectious particle. Unlike many other viruses, VV produces a multiplicity of virion forms, all of which appear to be infectious. Although the molecular details of poxvirus assembly and differentiation remain sketchy and controversial, the most widely accepted scenario of events which transpire is as follows. After (or concurrent with) viral DNA replication, assemblages of progeny DNA molecules, virion enzymes and structural proteins coalesce to form pre-virion particles. These particles acquire two membranes by budding through the intermediate compartment (between the endoplasmic reticulum and the Golgi) to become infectious intracellular mature virus (IMV). A portion of the IMV then becomes enveloped by two additional membranes derived from the trans-Golgi network to form intracellular enveloped virus (IEV). Following migration to the cell surface the outermost IEV membrane fuses with the plasma membrane to give rise to extracellular enveloped virus (EV). The EV can either remain associated with the cell (cell-associated enveloped virus, CEV) or be released into the external medium as extracellular enveloped virus (EEV). Some poxviruses, such as cowpoxvirus (CPV), produce yet another virion form. In CPV-infected cells, large inclusion bodies are produced which are composed primarily of a single 160 kDa viral protein. Within these A-type inclusions are occluded (and infectious) virions.

Considering the large number of viral encoded proteins, the multiplicity of VV virion forms and the number of distinct intracellular sites used during the viral assembly and morphogenesis process, one would predict that VV might utilize a number of the cellular protein modification and targeting pathways to regulate these complex processes. Indeed, it has been demonstrated that during the course of viral replication, VV proteins are matured by a number of posttranslational modifications including acylation, phosphorylation, glycosylation, ADP-ribosylation, and proteolytic processing. Although the details about what role limited proteolytic reactions might play during VV replication were not available when our studies were initiated in 1990, the information that was available in the literature suggested that both formative and morphogenic cleavage pathways might be employed. For example, both the VV growth factor (VGF) and hemagglutinin (HA) proteins appeared to have signal peptides removed via formative proteolysis during their transit through the endoplasmic reticulum and transport to the plasma membrane. Likewise, three of the major structural proteins found within the mature VV virion core, 4a, 4b and 25K, were known to be produced from higher molecular weight precursors at late times during infection, making them candidates for morphogenic cleavages. It was this latter question, namely the nature of the processing reaction by which the major VV core proteins are matured, that the experiments conducted in our laboratory over the last decade have addressed.

VV Proteolysis—What was Known Prior to 1990.

The genes expressed at late times during a VV infection (i.e., those expressed after the initiation of viral DNA synthesis) include most of the structural proteins required for the assembly of progeny virions. The first indication that some of the VV structural proteins might be subject to proteolytic processing occurred when Holowczak and Joklik noted differences in the apparent molecular weights of radioactively-labeled proteins present in VV-infected cells when compared to those found in purified virions. Subsequently, pulse-labeling of VV-infected cells was used to demonstrate that a large precursor protein could be chased into a smaller polypeptide, with concomitant disappearance of the larger-sized protein. This conversion could be specifically inhibited by rifampicin with no apparent effect on the synthesis of the precursor. The precursor protein was designated as P4a and the proteolytically processed product called 4a.

Additional pulse-chase experiments revealed that several other VV structural polypeptides, in addition to P4a, were apparently cleaved during the late phases of the VV replication cycle. These proteolytically processed proteins, referred to using the Sarov and Joklik designation of virion proteins, included 4a, 4b, VP8(referred to as 25K in our work), 9 and 10. This may in fact represent an underestimate of the number of VV late proteins which are subject to proteolysis. The VV core proteins 4a, 4b, and VP8 (25K) are the most abundant proteins in the VV particle, together constituting about 33% of the mass of the virion.

Tryptic peptide mapping and immunological reagents have been used to establish the relationships between the P4a, P4b and P25K precursors and their processed products 4a, 4b and 25K. Location of the three loci encoding these genes have been mapped and the nucleotide sequence of their open reading frames determined. With the completion of the sequence of the entire genome of the Copenhagen strain of VV, the genes encoding the P4a, P4b and P25K precursors received the designations A1OL, A3L and L4R, respectively. The proteolytic processing of VV structural proteins appears to be essential for the formation of infectious progeny virions. This conclusion stems from the observation that there are a variety of different drug treatments (e.g. rifampicin and α-amanitin) or conditional-lethal mutations in the genome, which apparently affect proteolysis (and particle maturation) without affecting overall protein synthesis.

SUMMARY OF THE INVENTION

The focus of the present invention is an effective antipoxvirus drug for use in treating or preventing human disease caused by pathogenic poxviruses. The target of our antiviral drug development efforts is the poxvirus proteinase responsible for core protein maturation, a step which is absolutely essential for the production and spread of infectious virions.

The present inventors have identified the viral gene product responsible for catalyzing core protein maturation, and have used genetic approaches to validate it as an antiviral target. Expression vector technology is used to express and purify the large quantities of the core protein proteinase. The purified proteinase can serve as the starting material for a two-pronged approach to the identification of potential inhibitors: 1) structure-function analysis coupled with rational drug design; and 2) development of an in vitro cleavage assay appropriate for use in high-throughput screening against limited libraries of potential proteinase inhibitors. Lead compounds identified by either approach will inhibit the replication of various orthopoxviruses in tissue culture cells. These compounds will be antiviral drugs useful to provide a rapid-response defense against the deliberate introduction of a pathogenic poxvirus into the environment.

In particular, the focus of the present invention is the development of an anti-orthopoxvirus drug which is potent, specific, can be produced or synthesized in a cost-effective manner, can be delivered orally, and whose mode of action is well understood. For this reason, we have selected the orthopoxvirus core protein proteinase (vCPP) as our target for drug development. The present inventors have identified the cysteine proteinases encoded by the I7L and G1L genes as vCPPs. The role of these enzymes in the orthopoxvirus replicative cycle is relatively well understood; they appears to have unique substrate recognition sites; and the requirement for these enzymes is conserved amongst all orthopoxviruses.

BRIEF DESCRIPTION OF THE DRAWING FIGURES

FIG. 1. Transient Expression of I7L enzyme with P25K:FLAG substrate in $BSC_{40}$ cells. Cells were infected with wildtype vaccinia virus and transfected with either pRB21:I7L, P25K:FLAG, or a combination of these and cleavage of the P25K:FLAG substrate was determined by Western blotting using anti-flag mAB. The P25K:FLAG substrate is shown alone in lane 4 and is probably slightly cleaved by the virally produced I7L protease. I7L is shown to cleave the 28 kDa substrate into a 25 kDa product (lane 5).

FIG. 2. Transient Expression of I7L enzyme with P25K:FLAG substrate in $BSC_{40}$ cells. Cells were infected with ts16 virus and transfected with either pRB21:I7L, P25K:FLAG, P25K:FLAG:IDI, P25K:FLAG:RPD, pRB21:I7L:mut, or a combination of these and cleavage of the P25K:FLAG substrate was determined by Western blotting using anti-flag mAB. The P25K:FLAG substrate is shown alone in lane 4. I7L is shown to cleave the 28 kDa substrate into a 25 kDa product (lane 5). The P25K IDI mutant (mutated at the AGS site) is cleaved by I7L (lane 6) and the RDP mutant (mutated at the AGA site) shows cleavage at another site (AGS) (lane 7). The I7L-mutant lost its ability to cleave the substrate (lane 8).

FIG. 3. Pulse-chase labeling and immuoprecipitation of VV core proteins.

FIG. 4. Alignment of determined AA sequence of VV 4b (SEQ ID NOS 27 and 28) and 25K (SEQ ID NOS 25 and 26) proteins versus their precursors.

FIG. 5. Alignment of the predicted AA sequences surrounding the cleavage sites of VV and FPV proteins (SEQ ID NOS 29–44, respectively in order of appearance).

FIG. 6. Proteolytic processing pathway of the VV 4a core protein precursor.

FIG. 7. Summary of proteolytic cleavage in VV AG*A-containing substrates.

FIG. 8. Interconversion of VV previrions. VV-infected cells were labeled with 3H-thymidine until 7 hours post infection then chased for 0 (A), 5(B), 11(C), or 17(V) hours before harvesting. Extracts were subjected to sucrose log gradient fractionation, and the fractions were assayed for cold acid-precipitable radioactivity.

FIG. 9. Structure and cleavage sites of the P25K:FLAG reporter gene. Both the primary AGA(II) and secondary AGS(I) cleavage sites are noted (SEQ ID NOS 45–47).

FIG. 10. Mapping of the G1L ORF as the complementing proteinase by transient expression.

FIG. 11. Alignment of the proposed active-site residues of G1L proteinase and several insulin-degrading enzymes and other zinc metalloproteinases (SEQ ID NOS 48–54, respectively in order of appearance).

FIG. 12. Inhibition of VV replication by 1 μM 1,10 phenanthroline (A) and 10 μM iodoacetamide (B). The squares indicate presence of drug, the diamonds the control infections.

FIG. 13. Electron micrograph of VV at 8 hours post-infection. The panel on the right is mature infectious virions from the control infection. The panel on the left contains non-infectious immature particles that accumulate in the presence of α-amantin.

FIG. 14. FPA assay. A peptide will be synthesized with a fluorescence group on the amino terminus and a quench group on the carboxyl terminus. Following cleavage, the fluorescence emission will increase due to the lack of proximity between the fluor and the quench.

FIG. 15. HTRF assay. A cleavage site peptide will contain a biotin group on the N-terminus that will be conjugated with XL665-stretavidin. The C-terminus will have an oligo-histidine (SEQ ID NO:63). Addition of α-his conjugated to caged Europium cryptate will allow fluorescent resonance energy transfer (FRET) between Eu-cryptate and XL665. Cleavage will inhibit FRET.

FIG. 16. VV Core Protein Cleavage sites. Schematic representation of the three major core protein precursors. The positions of the AGX cleavage sites are indicated with the amino acid number of the Gly.

FIG. 17. Proteolytic processing of P4b polyprotein by I7L. $BSC_{40}$ cells were infected with ts16 VV and transfected with plasmids containing the I7L and P4b genes respectively. Cells were harvested 24 h post-infection and the extracts analyzed by Western blot with anti-Flag antisera. Lane 1, cells infected with ts16 alone; lane 2, cells infected with ts16 and transfected with P4b; lane 3, cells infected with ts16 and cotransfected with both P4b and I7L plasmids; lane 4, cells infected with ts16 and cotransfected with P4b and pI7LH241A (see Table 1); lane 5, cells infected with ts16 and transfected with P4bIDI; lane 6, cells infected with ts16 and cotransfected with P4bIDI and pI7L; lane 7, cells infected with ts16 and cotransfected with P4bIDI and pI7LH241A;. The bands corresponding to the precursor protein P4b and its mature cleavage product 4b are indicated on the right. Molecular weight is indicated on the left.

FIG. 18. Proteolytic processing of P4a polyprotein by I7L. $BSC_{40}$ cells were infected with ts16 VV and transfected with plasmids containing the I7L and P4a genes respetively. Cells were harvested 24 h post-infection and the extracts analyzed by Western blot with anti-Flag antisera. Lane 1, uninfected cells; lane 2, cells infected with ts16 alone; lane 3, cells infected with ts16 and transfected with P4a; lane 4, cells infected with ts16 and cotransfected with both P4a and I7L plasmids; lane 5, cells infected with ts16 and cotransfected with P4a and pI7LH241A; lane 6, cells infected with ts16 and transfected with P4aIDI617; lane 7, cells infected with ts16 and cotransfected with P4aIDI617 and pI7L; lane 8, cells infected with ts16 and cotransfected with P4aIDI617 and pI7LH241A; lane 9, cells infected with ts16 and transfected with P4aIDI697; lane 10, cells infected with ts16 and cotransfected with P4aIDI697 and pI7L; lane 11, cells infected with ts16 and cotransfected with P4aIDI697 and pI7LH241A. The bands corresponding to the precursor protein P4a and the small cleavage products are indicated on the right. Molecular weight is indicated on the left.

FIG. 19. Characterization of I7L. Predicted hydrophobicity plot of the I7L protein using Kyte-Doolittle program. Positions of the putative catalytic triad (H241, D248, C328) as well as the ts16 mutation and the mutation of the histidine residue to inactivate I7L are indicated with arrows. The positions of the amino acids are indicated underneath. Sequence homology to the same gene in Variola virus, Camelpox virus, and Monkeypox virus are indicated underneath by rectangles with positions of differing amino acids indicated at the correct position by a black bar. Sequence homology of the conserved catalytic domain between VV I7L (SEQ ID NOS 55 and 56), the ASFV protease (SEQ ID NOS 57 and 58), adenovirus protease (SEQ ID NOS 59 and 60), and a yeast cysteine protease (SEQ ID NOS 61 and 62) is indicated in the bottom of the figure with arrows pointing at the highly conserved amino acids.

FIG. 20. Proteolytic processing of P25K, P4a, and P4b by mutant I7L

FIG. 21. Marker rescue of ts16 with full length I7L, truncated I7L, and mutant I7L

DETAILED DESCRIPTION OF THE INVENTION

Figure 1:
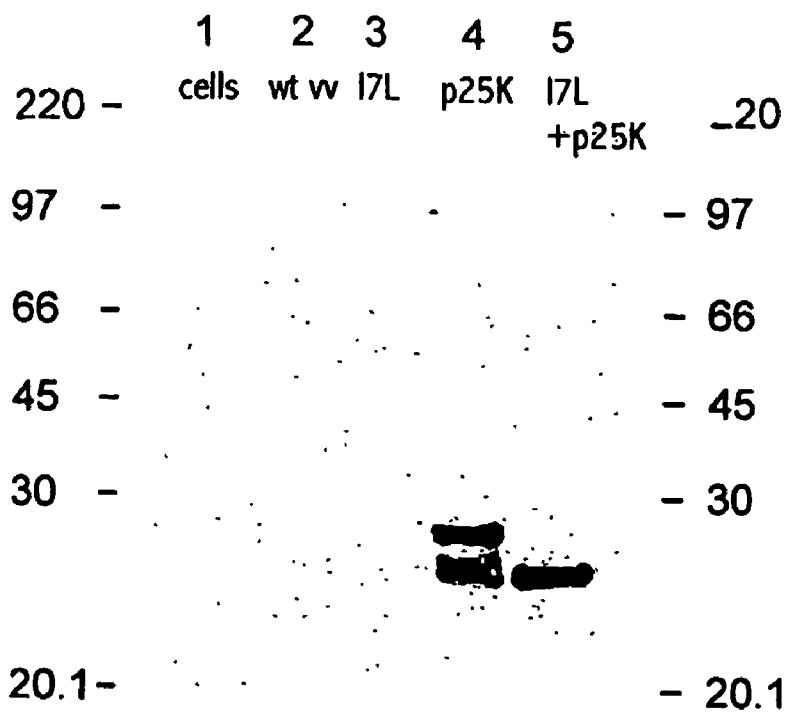

The present invention provides means to discover and develop compounds capable of inhibiting the growth of pathogenic orthopoxviruses (such as smallpox) and disease-associated pathology in the human host.

Development of an effective antiviral drug requires the identification of a specific interaction or activity whose disruption will be lethal to the virus and relatively benign to the host. Since viruses, such as orthopoxviruses, are obligate intracellular parasites which utilize many of the host cell enzymes and metabolic pathways during their replication, this task is often quite difficult and this fact is chiefly responsible for the relative paucity of successful antiviral drugs. The drugs that have proven effective, such as acylcovir, are typically directed against nucleotide metabolizing or biosynthetic enzymes. Since many of the orthopoxvirus-encoded enzymes involved in nucleic acid biosynthesis are highly homologous to their mammalian counterparts (for example, vaccinia virus thymidine kinase shares more than 90% identity with the human enzyme), it has previously proven difficult, if not impossible, to identify compounds that specifically block these viral enzymes.

Most viruses use proteolysis catalyzed by viral-encoded proteinases as a key step in their developmental cycle, opening up a new class of targets for antiviral drug development. Recently, proteinase inhibitors have been developed that specifically target HIV, hepatitis C virus and influenza enzymes which have proven very effective at preventing disease in the human host. Thus, it is of particular interest to note that proteolytic maturation of orthopoxvirus core proteins is absolutely required for infectious progeny to be produced. Studies in our laboratory over the past ten years have identified the unique cis signals required to direct endoproteolytic cleavage of core protein precursors, established the contextual requirements of core protein maturation, and suggested strongly that the proteinase which carries out this essential reaction is viral-encoded. The present invention takes advantage of this attractive target and our extensive experience working on this problem, to develop an effective antiviral drug that blocks orthopoxvimus replication based on specific mechanistic inhibition of the viral core protein proteinase (vCPP).

In particular, the present invention provides:

1. The vCPP responsible for orthopoxvirus core protein maturation.

2. The use of conditional-lethal genetic approaches to validate vCPP as an essential gene product.

3. The use of mammalian and/or prokaryotic expression vector technology to enable the production and purification of large quantities of vCPP.

4. Structure-function and biochemical analyses of purified vCPP.

5. An in vitro cleavage assay to measure vCPP enzyme activity, and the use of that assay in mechanism-based high-throughput screening procedures against sub-libraries of potential proteinase inhibitors.

6. Demonstration of lead compounds that inhibit the replication of various orthopoxviruses in tissue culture cells, due to blocking vCPP activity.

The present invention provides a means of identifying anti-poxvirus compounds that are very specific in their inhibitory profile against vCPP, are highly potent so low concentrations are required, and have chemical characteristics that provide excellent bioavailability without causing generalized toxicity. Such compounds are also easy and economical to synthesize, present no unusual formulation problems and are stable so as to provide a long shelf-life.

Expression and Purification of vCPP.

Production of a monospecific polyclonal antisera makes it possible to follow the intracellular synthesis and fate of the vCPP protein, and to support purification and assay development.

The entire vCPP ORF (with or without an oligohistidine tag) may be expressed in expression vectors for use as a source of immunogen to induce an antiserum with broad reactivity that recognizes multiple epitopes within the intact protein. Prokaryotic expression vectors may be used; however, since vCPP is a proteinase, the expression of this activity in bacterial cells can be lethal and prevent isolation of the clone of interest. Should this problem arise, two alternative methods may be employed. First, it is possible to employ expression vectors in which expression of the foreign insert is under very stringent control, to minimize expression in the absence of induction, and purify the vCPP at early times post induction before the expressing cells are killed. Second, an inactive form of the vCPP protein can be cloned and expressed.

Mutation of the residues within the HXXEH motif is known to inhibit G1L enzyme activity. Similar mutations can be introduced into the potential catalytic diad(s) of I7L. Subdomain-specific antisera can also be generated, either by using prokaryotic expression vectors to produce in-frame fusion proteins containing only small portions of the vCPP protein, or by synthesizing synthetic peptides corresponding to these regions (coupling the peptides to carrier proteins, if necessary). Both of these approaches have been used successfully to obtain region-specific antisera against several of the VV core proteins. Computer analyses of the G1L and I7L ORFs suggest that there are potential immunogenic epitopes located throughout the proteins, with many of these predicted to be located on the surface of the protein. In addition to being of use in the in vivo experiments, subdomain-specific antisera should be useful for probing the catalytic and binding domains of the vCPP protein.

If additional immunological reagents are required to probe the structure of vCPP, purified vCPP protein can be used as an immunogen in the production of monoclonal antibodies. In any case, the immunoreactivities of all of the derived sera can be mapped and confirmed by using a genetically-engineered nested set of vCPP protein truncations or by the BIAcore technique.

In order to overproduce enzyme for biochemical characterization and for use in assay development, the vCPP protein can be overexpressed in both eukaryotic and prokaryotic cells, purified and characterized. One source of the vCPP protein is from the VV-infected mammalian cell. Expression in mammalian cells has the advantage that any potential posttranslational modifications, catalyzed by either cellular or viral enzymes, will occur. Although it is possible that sufficient quantities of the vCPP protein could be isolated from a wild-type VV infection carried out in the presence of rifampicin to block processing, recent advances in VV vector technology make it possible to overexpress the vCPP protein without difficulty.

The ORF expressing the vCPP can be inserted into a plasmid vector downstream of the T7 promoter and EMC translational enhancer. This plasmid may then be transfected into recipient mammalian cells that are superinfected with a VV(MVA strain):T7 recombinant. Under these conditions, the genomic copy of the T7 RNA polymerase gene is expressed, which drives high level expression of the vCPP protein from the plasmid. However, since the MVA strain of VV is unable to complete its replicative cycle in mammalian cells, contextual processing of the VV core proteins will be aborted, so the vCPP protein will accumulate. Alternatively, commercially available baculovirus expression vectors may be employed. Although they are not glycosylated (which is unlikely in the case of vCPP), mammalian proteins produced in insect cells are usually functional.

To overexpress vCPP protein in prokaryotic cells, the SPEX System can be used. This is a protein expression vector that uses nonpathogenic, GRAS (Generally Regarded As Safe) gram-positive bacteria, such as various *Streptococcus* or *Lactococcus* sp., to produce and export proteins. This system is described in U.S. Pat. No. 5,821,088, the contents of which are incorporated herein by reference. The SPEX system takes advantage of a conserved pathway that all Gram-positive bacteria utilize to export and anchor proteins on the cell surface. Heterologous proteins are directed to be expressed on the cell surface of the Gram-positive host or secreted into the culture medium by using portions of the M protein, a fibrillar surface protein of *Streptococcus pyogenes*, as a fusion partner.

The signal sequence and propeptide sequence from the M protein are fused to the gene product of interest to achieve translocation through the cell membrane of the Gram-positive host cell which results in the direct secretion of the desired protein into the culture medium. Some advantages of this vector system that make it well-suited for prokaryotic production of the vCPP include: 1) recombination vector cloning manipulations use standard *E. coli* methodology; 2) one-step selectable transfer of the recombination vector into SPEX expression strains; 3) choice of chromosomally-integrated or plasmid-based expression; 3) GRAS expression vector strains (should be more amenable to producing GLP lots of enzyme); 4) no release of toxic intracellular products such as LPS; 5) protein products are produced in a soluble form and can assume active conformation (unlike many proteins produced in *E. coli* which form insoluble inclusions in the periplasm); 6) no apparent size limitation of protein products expressed ($\geq$150 kDa); 7) low production cost in simple laboratory media lacking bovine products (no potential for BSE contamination); 8) good yield, 3–5 mg of protein per liter of bacterial culture without optimization; and 9) can be scaled up for manufacturing because Gram-positive bacteria are amenable to high density fermentation. Using this system, we have already achieved expression of a large number of antigenically-authentic and enzymatically-active foreign proteins vCPP protein from both mammalian and bacterial sources can be purified using a combination of traditional and/or immunoaffinity chromatographic procedures. It is recommended to work quickly, to work in the cold, and to store chromatographic fractions under conditions likely to facilitate maintenance of enzymatic activity (e.g., adding glycerol and/or keeping protein concentrations high). In order to further enhance the ability to purify the vCPP, the eukaryotic and prokaryotic expression vectors may be re-engineered so that the vCPP protein is expressed with a short oligo-histidine tract fused to its N- or C-terminal. The his-tagged G1L and/or I7L proteins can then be purified directly via metal-affinity chromatography, using art-known methods.

The addition of 6–10 histidine residues at either end of the vCPP protein will not affect its enzymatic activity. It has previously been demonstrated that the addition of a histidine-tag to the N-terminus of the sortase or speB proteinases of *S. pyogenes* has no demonstrable effect on the ability of the protein to carry out catalysis on its natural substrate. Likewise, scientists have successfully developed purification protocols for SpeB, sortase and DegP proteinases.

vCPP Cleavage Assay.

Despite the fact that proteolysis of VV core protein precursors occurs in vivo only within the context of the assembling virion, the present inventors have established a cleavage assay for use in conjunction with rational drug design and/or HTS. This assay is based on our ability to develop in vitro cleavage assays for a variety of other viral proteinases that also participate in morphogenic cleavage reactions. Having purified vCPP proteinase in hand, a suitable substrate is identified, a useful format is designed, and conditions are developed that favor specific endoproteolytic cleavage of the AG(X) motif. Specific cleavage assays for the SpeB, sortase and DegP enzymes are already established, and similar approaches are used here. Below are outlined three different types of assays, presented in order of complexity and potential utility in subsequent drug development.

a) ELISA. A peptide comprising the AG(X) motif, and optionally further comprising surrounding amino acids from the P4b cleavage site, is provided. The peptide is labeled. The label may be a fluorescent tag, such as IAEDANS or Didansyl-L-cysteine (Molecular Probes, Oreg.), linked to one terminus of the peptide, such as the amino terminus. The peptide is applied to a pre-activated microtiter plate, and allowed to incubate, e.g., overnight, followed by a blocking solution to coat the reactive surface of the plate. vCPP is added to the plate and the extent of cleavage monitored with time by the release of fluorescence as monitored using, for example, a TECAN microfluorimeter. Alternatively, an immunological readout may be employed, using a standard ELISA format together with cleavage site specific antisera as the primary antibody.

b) FPA (Fluorescence proximity assay). This assay is based on a fluorescence-quench pair of probes that are conjugated to the $NH_2$ and COOH ends of the peptide. With the quench group in dose proximity to the fluorescent group, such as prior to deavage, the fluorescence energy is absorbed by the quench group resulting in a relatively low or baseline signal. Following cleavage of the peptide by the protease, the quench group is "removed" from the immediate vicinity of the fluorescent group and the fluorescence of the probe is elevated over baseline. This is a very sensitive assay and is in the optimal format, so-called "mix and measure," for HTS.

A peptide is provided that comprises the defined AG(X) cleavage site with a dabcyl succinimidyl ester (dabcyl) group conjugated to one terminus, and an EDANS group, 5-(2-aminoethyl)amino)napthalene-1-sulfonic acid, conjugated to the other terminus. In one possible embodiment, the dabcyl group is conjugated to the $NH_2$-terminus, while the EDANS group is conjugated to the COOH-terminus. Dabcyl has no fluorescence properties but a strong absorbance that overlaps the peak emission spectra of EDANS. This peptide is titrated into wells of black view plates and then vCPP protease added. An increase in fluorescence indicates cleavage of the peptide.

c) HTRF. A peptide similar to that described for the EPA assay is synthesized to include the AG(X) cleavage site and modifications at either end to allow for labeling with the reagents required for the resonance energy transfer. The amino-terminus of the peptide is biotinylated and the carboxyl-terminus has a poly-histidine tag. The HTRF assy is dependent on the fluorescent-resonance energy transfer (FRET) from an excited Europium cryptate (Eu cryptate) group to a modified allophycocyan in (XL665). Streptavid in, which is commercially available, may be used to modify the amino-terminus and a commercially available Eu cryptate-coupled anti-His6 antibody (6×His tag disclosed as SEQ ID NO:63), (Packard Bioscience Co, Meriden, Calif.) to modify the carboxyl-terminus of the peptide. When this reagent is excited at 337 nm the Eu-cryptate, due to proximity, transfers energy to XL665. The XL665 then loses energy, emitting light at 665 nm. Following cleavage of the peptide, resonance energy transfer from the excited Eu-cryptate to the XL665 does not take place and the resulting emission signal at 665 nm is reduced.

Rational Drug Design of vCPP Inhibitors.

One of ordinary skill in the art will readily be able to use whatever assay format is preferred, and can vary reaction conditions (protease:substrate ratio, ionic strength, temperature, hydrophobicity, etc.) in order to optimize the reaction. Validation that cleavage is occurring at the anticipated site can be obtained by microsequence analysis of cleavage products, use of peptide substrates containing mutated cleavage sites, and inclusion of proteinase inhibitors specific to the predicted class of proteinase to which vCPP belongs. Likewise, the antisera generated above can be used in conjunction with these assays to map interactive surfaces and active sites of the enzyme.

Structural analyses of the protein can also be conducted as an approach to determining its three-dimensional structure. By subjecting purified enzyme to analytical procedures such as CD (circular dichroism), two-dimensional NMR (nuclear magnetic resonance), or crystallization/X-ray diffraction a great deal of structural information can be quickly obtained about vCPP. That information, coupled with the identification of the catalytic residues, and the knowledge of the class of proteinase to which vCPP belongs, permits structural modeling to be carried out. Using such information, one of ordinary skill will be able to identify subsets of chemical entities that are likely to bind to a proteinase of a given class with certain chemical characteristics. This chemical subset can be used as a starting point and to test the probable inhibitors in our cleavage assay. Any which score as positive can serve as the starting point for subsequent iterative chemistry.

vCPP HTS.

One of the most powerful and useful techniques for identification of useful chemical entities in the pharmaceutical industry is automated high-throughput screening. Most of the drugs that are available and many of those currently in development have been discovered in this manner. Unfortunately, random HTS versus either random natural compounds or combinatorial chemistry is slow, expensive and very labor intensive.

One of ordinary skill in the art will readily be able to use one of the assay formats described above, such as a mix and measure approach such as FPA or HTRF, to manually screen chemical library subsets that have been selected as potential proteinase inhibitors. One of the utilities of HTS is that for any potential inhibitor that is identified, one can quickly establish effective concentration ranges and test specificity against other proteinases, and do so in a replicate fashion.

In vivo Screen for vCPP Inhibitor Activity.

Lead compounds identified by rational drug design or HTS can be tested for in vivo efficacy in the following manner:

a) Increasing concentrations of lead compounds are placed on uninfected tissue culture cells from several different species, L-929 (murine), RK-13 (rabbit), RL-1 (rat), HeLa (human) and $BSC_{40}$ (monkey). Cells are observed for morphological alterations, growth rate, DNA synthesis and viability as measured by exclusion of the vital dye Trypan Blue.

b) Increasing concentrations of the lead compounds are placed on $BSC_{40}$ cells infected with VV. The infected cells are analyzed for the production of infectious virus, viral protein synthesis, viral DNA synthesis, status of virion assembly and core protein cleavage as described above. If the inhibitor is specifically targeting vCPP, an abortive-late phenotype will be observed.

c) For a vCPP inhibitor to have potential as a antiviral drug, it should be effective against a variety of orthopoxviruses. Therefore, the vCPP inhibitor is tested against a variety of VV strains (WR, IHD, Copenhagen), rabbitpox, and cowpox. In addition, any promising inhibitor is tested against non-orthopoxviruses such as fowlpox, orf, ectromelia and entomopoxvirus to determine the breadth of inhibition.

EXAMPLES

As an experimental system, the present invention uses the vaccinia virus (VV) because of the wealth of available information in the art, the proven ability to grow and manipulate it in the laboratory, acceptable biosafety profile, and because of the high level of functional and sequence conservation with variola virus.

Example 1

The I7L open reading frame in vaccinia virus encodes a 423 amino acid cysteine protease containing the conserved catalytic triad (His241, Asp248, Cys328) indicative of these proteases. It also contains an invariant glutamine (Q) residue just upstream of the cysteine residue predicted to help form the oxyanion hole in the active site. The I7L protein is believed to be the core protein protease for vaccinia virus.

Figure 2:
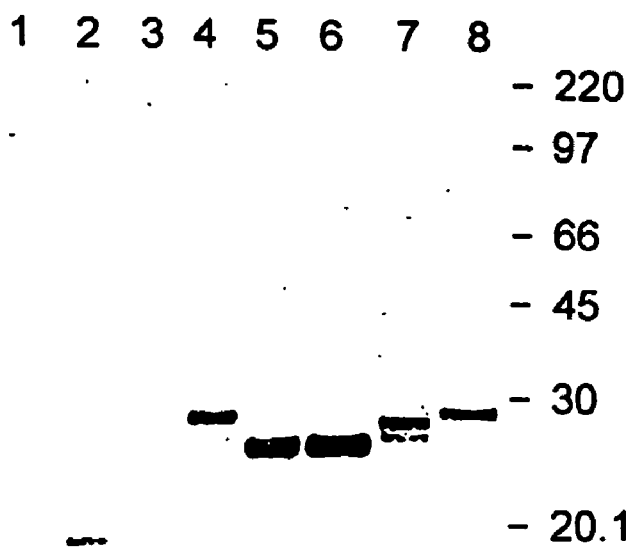
Figure 3:
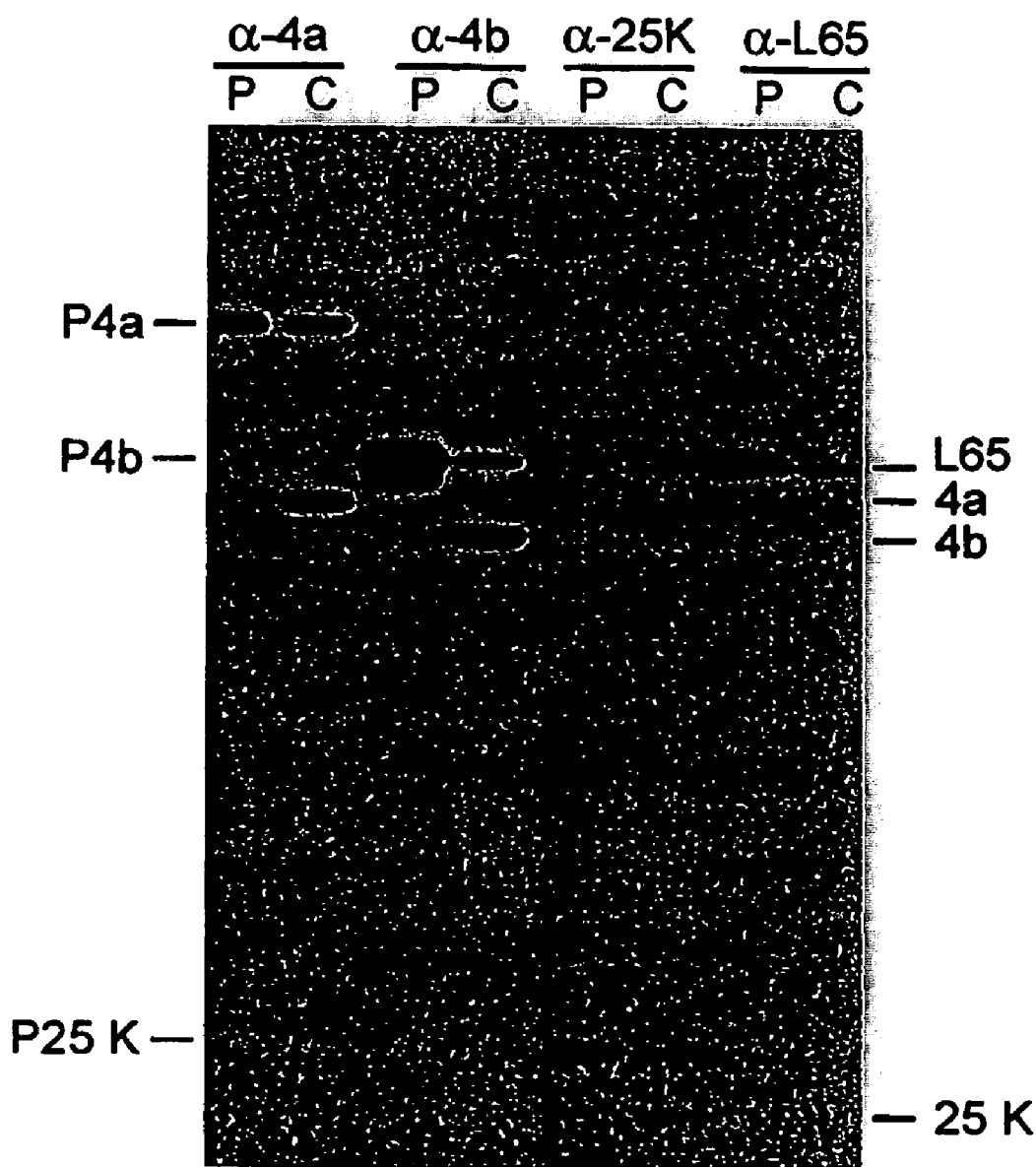

Possible substrates of the core protein protease are P4a, P4b, P25K, P21K and P17K (2), which are all proteolytically processed. Alignment of the cleavage sites in these precursors reveals a conserved AG*X cleavage motif. For the experiments described below, P25K was chosen as the test substrate. P25K contains two putative cleavage sites, AGS at amino acids 17–19 and AGA at amino acids 31–33. In order to determine if I7L is the core protein proteinase, I7L fused to a C-terminal 6× Histidine tag (SEQ ID NO:63) and P25K fused to a C-terminal FLAG tag were cloned Into plasmids for transient expression studies in vaccinia virus. Both plasmids were transfected into $BSC_{40}$ cell with vaccinia virus. Western blot analysis using FLAG-specific M2 antibody showed that when I7L and P25K were co-expressed the P25K substrate was cleaved producing a 25 KDa band (FIG. 1, lane 5 and FIG. 2, lane 5).

To further characterize the cleavage site, two mutations were made in the P25K open reading frame altering the amino acids at the two cleave sites by site-directed mutagenesis. The first mutant has amino acids 17–19 changed from AGS to IDI. The second mutant has amino acids 31–33 changed from AGA to RDP. The ability of the mutant proteins to be processed was analyzed by transient expression in VV-infected cells. As demonstrated by immunoblot using FLAG-specific M2 antibody, when the IDI mutant plasmid is co-expressed with I7L, cleavage is still observed (FIG. 2, lane 6), showing that I7L is cutting at the AGA site. However, there is partial cleavage of the RDP mutant (FIG. 2, lane 7), which could mean that I7L can cut at the AGS site as well. From these results, it is possible that P25K undergoes a two-step proteolytic process of cleavage at the AGS site and then cleavage at the AGA site. The results presented herein show that I7L is able to cleave P25K at the AGS and AGA sites and process the precursor protein from a 28 KDa protein to a 25 KDa protein.

We have demonstrated that a large number of VV core proteins, including 4a, 4b and 25K, appear to be processed via a common morphogenic cleavage pathway that is intimately linked with virion assembly and maturation. These substrates are synthesized as precursors during the late phase of viral gene expression. The precursor form is essential for the proteins to be targeted to the virus factory and to become associated with the assembling virion. Cleavage of the precursors occurs only within the context of the maturing virion. All of the precursor proteins appear to be cleaved at a novel AG(X) motif. This motif is distinct from that utilized in any other viral system and it is not recognized by any known proteinase. The enzyme responsible for these cleavages has been identified as a VV late protein and appears to be the I7L encoded cysteine proteinase.

Example 2

Identification of P4b and P25K Cleavage Sites—the AGA Motif

By pulse-labeling VV-infected cells after the onset of viral DNA synthesis and analyzing the extracts by SDS:polyacrylamide gel electrophoresis and autoradiography, three major radiolabeled protein species with apparent molecular weights of 95 KDa (P4a), 65 KDa(P4b) and 28 Kda(P25K) are observed. Upon addition of media containing an excess of unlabeled amino acids and with continued incubation of the infected cells, these three proteins are chased into 62 KDa (4a), 60 KDa(4b) and 25 KDa (25K) species that cemigrate with the three major virion core proteins. Interestingly, unlike many proteolytic reactions, the conversion process is not rapid with a delay of about 30–45 minutes observed between the time of precursor synthesis and the appearance of cleavage product. Furthermore, proteolysis of the VV core protein precursors appears to require ongoing de novo protein synthesis as addition of cycloheximide at the time of the chase completely inhibited product formation. Both of these observations are in agreement with the hypothesis that cleavage occurs within the context of an assembling virion, a process which requires both time and continual protein synthesis. This was our initial basis for proposing the "contextual processing" hypothesis of VV core protein proteolysis.

Figure 4:
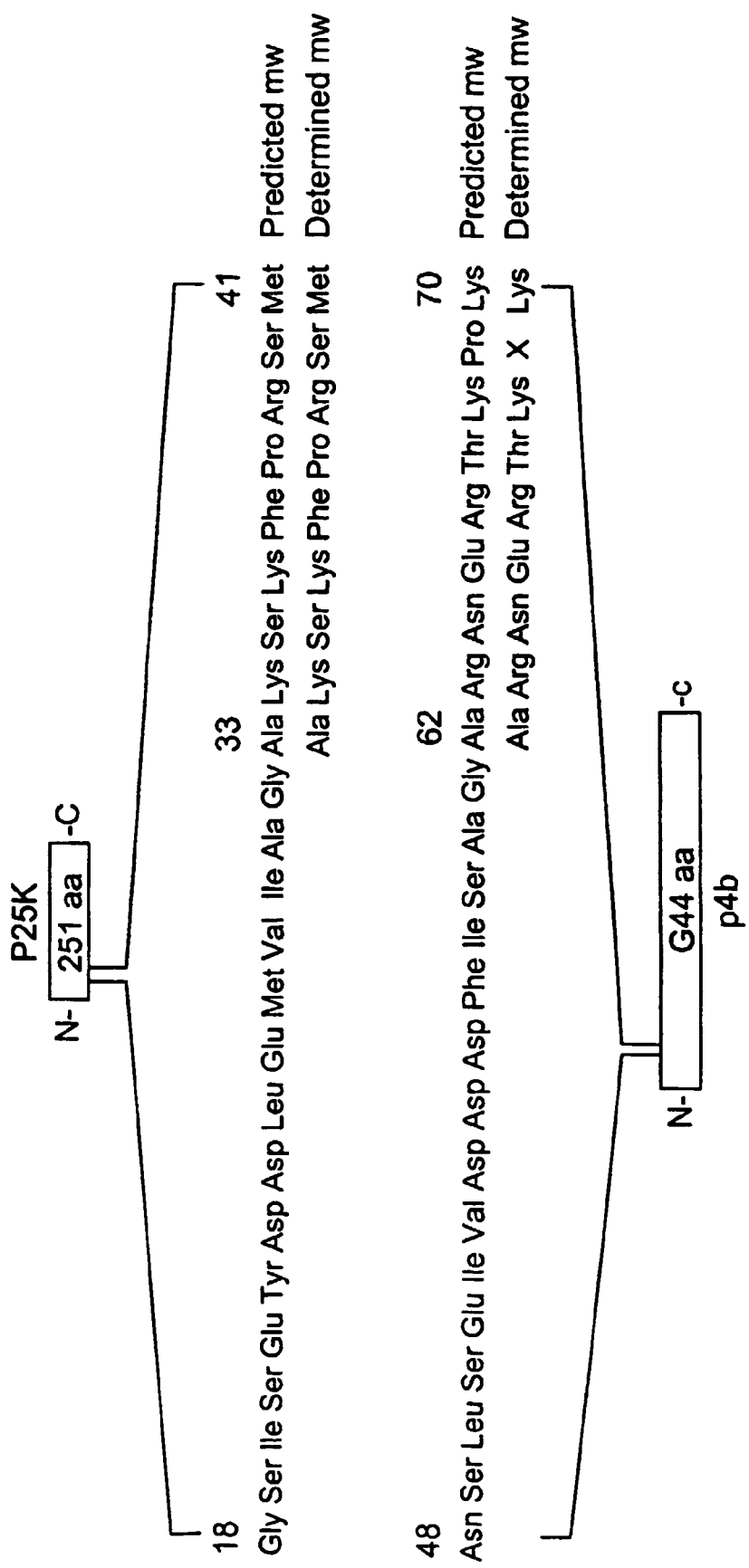
Figure 8:
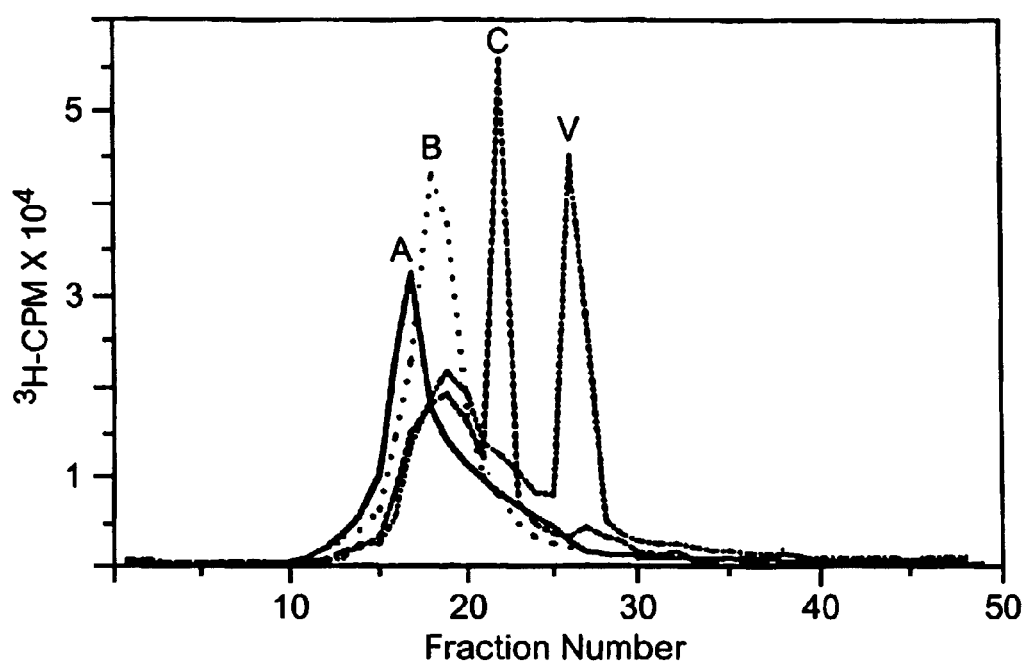

To determine the sites at which the VV core protein precursors were being cleaved, mature 4a, 4b and 25K proteins were isolated, purified and subjected to N-terminal microsequence analysis. The derived sequence was then compared to the predicted amino acid sequences of the P4a, P4b and P25K ORFS. The amino termini of the 25K and 4b proteins were identified as residue 33 of P25K and residue 62 of P4b, respectively (FIG. 4). The predicted decrease in molecular weight due to the loss of 32 and 61 amino acids from the N-terminus of P25K or P4b, respectively, corresponded well with the shift in migration observed in gels following proteolytic processing. Since neither of the small peptides were isolated, it could not be determined if the processing of the P4b and P25K precursors proceeded via an endoproteolytic cleavage, exoproteolytic digestion, or a combination of the two processes.

Comparison of the predicted amino acid sequences within the P4b and P25K precursors which surround the derived N-termini of the mature 4b and 25K proteins revealed the presence of an identical motif. The N-termini of both cleavage products were found within a conserved Ala-Gly-Ala (AGA) tripeptide, with the predicted cleavage site occurring at the Gly-Ala scissile bond. The importance of the AGA motif as a cleavage site determinant was suggested by two lines of evidence. First, there were no other apparent sequence elements conserved upstream or downstream of the putative P4b and P25K cleavage sites.

Second, although the fowlpox virus (FPV) 4b and 25K core protein homologs only shared 52% and 33% identity, respectively with the VV proteins (50), both FPV precursors contained an AGA motif at exactly the same location as the VV core protein precursors (FIG. 5). Interestingly, although the 4a protein was subjected to similar analyses, no microsequence data was obtained, suggesting that its N-terminus was blocked.

Example 3

P4a Maturation Pathway

The predicted amino acid sequence of the P4a precursor does not contain the conserved AGA tripeptide motif utilized in the processing of P4b and P25K. This raised the possibilities that the P4a protein was processed by a different pathway, or that P4a was processed by the same pathway as P4b and P25K but at sites that were less efficiently cleaved.

Support for this hypothesis was drawn from the observation that cleavage of the P4a precursor seems to proceed at a slower rate than that of the P4b and P25K precursors in vivo (51). With that in mind, the predicted amino acid sequence of the 891 amino acid P4a precursor was searched for the sequence AGX and three signals were found, AGN (residues 94–96), AGS (residues 613–615) and AGT (residues 696–698). If cleavage occured at all three sites within the P4a precursor, an internal protein of approximately the correct size for 4a would be released.

To test the hypothesis that the VV core protein 4a was cleaved from P4a by proteolysis at the three internal AGX sites, immunological reagents which were specific for subregions of the P4a precursor were generated and used in concert with a variety of peptide mapping and protein sequencing procedures. The results obtained demonstrated that the P4a precursor was cleaved at two locations, the AGS site between residues 613 to 615 and the AGT site between residues 697 and 698. Both the large N-terminal 4a protein (residues 1 to 614) and the C-terminal 23 KDa protein (residues 698 to 891) become major virion core constituents. The location and fate of the small internal peptide predicted to be released (residues 615–697) is not known. However, using site-directed mutagenesis, mutant P4a proteins were produced in which either the AGS or AGT sites had been genetically inactivated. Using transient expression procedures, it was possible to demonstrate the existence of the 4a–9K or 9K–23K chimeras in vivo, suggesting that the internal 9 KDa sequence is not inherently unstable. Furthermore, the ability to isolate and microsequence both endproducts from cleavage at the AGS and AGT sites also strongly suggested that processing was occurring via a single endoproteolytic cleavage event. Although the internal AGS and AGT sites of the P4a precursor were cleaved, two independent lines of peptide mapping data clearly demonstrated that the AGN site at residues 94 to 96 was not processed. Thus, these results suggest that processing of all three major core protein precursors is likely to be coordinately linked and catalyzed by the same viral proteinase during viral assembly, with the endoproteolytic cleavage occurring at an internal AGX motif (where X can be A, S or T, but not N).

Example 4

The AG(X) Cleavage Motif

All three of the VV core proteins that were known to be proteolytically processed are cut at AGX motifs. It was therefore of interest to ask within the context of the entire VV genome, how many times an AGX tripeptide is predicted to be present in a VV protein, and to determine the frequency at which the motif is utilized as a cleavage site. Using the complete nucleotide sequence of the VV (Copenhagen) genome (49), the predicted amino acid sequence of each ORF was determined and compiled into a single database. A search of this database for the AGX tripeptide revealed it occurred 82 times among the 198 major ORFS, which is substantially less frequent than the 204 sites expected if AGX occurred randomly. Of these 82 sites, 18 resembled sites that had previously been shown to be actively cleaved, namely AGA of P25K and P4b, and AGT and AGS of P4a.

To explore whether some or all of these AGX motifs serve as cleavage sites during VV replication, we focused our attention on the AGA tripeptide as a test case. The AGA motif occurs seven times. The proteins containing the AGA motif are: P4b and P25K core protein precursors (both of which are cleaved), the A12L and A17L gene products of unknown function, the palmitylated P37 protein encoded by the F13L ORF which is found in the outer membrane surrounding EEV particles, the VV DNA polymerase (DNAP) encoded by the E9L ORF, and host range (HR) protein encoded by the KIL gene. To determine if these proteins were processed during the course of a VV infection, monospecific antisera were produced or obtained (αDNAP from P. Traktman and αP37K from R. Wittek) for each individual gene product and used in concert with pulse-chase radiolabeling and immunoprecipitation procedures.

The results obtained clearly indicated that the DNAP, P37K and HR proteins were not proteolytically processed. In contrast, the gene products of the A17L and A12L ORFs were synthesized as 23 KDa and 24 KDa precursors which were processed to 21 KDa and 17 KDa products. The processing reaction was inhibited by rifampicin and the processed products were found in association with the virion particle, suggesting that the A17L and A12L gene products were being matured by the same pathway as the P4b and P25K precursors. These results allowed us to propose several rules governing the morphogenic cleavages in VV (FIG. 7)

To be processed, a precursor protein must: 1) Contain a AGA (or AGX) motif; 2) be expressed at late times during infection (DNAP is an early protein, HR is an early-immediate protein); and 3) be destined for incorporation into the virion core (P37 is a late protein but is located in the membrane not the core). Even with these stringencies, given the number of AGX occurrences plus the large number of proteins found in the complex VV virion, this suggests that as many as 40 to 50 viral proteins may be subject to morphogenic cleavages during virion assembly.

Having proposed these rules governing morphogenic proteolysis caused us to re-examine the processing of the A12L gene product. This gene product is expressed at late times. It is apparently a core protein. And it contains not one but three AGX motifs. In addition to the AGA tripeptide near the N-terminus of the 23 KDa A12L precursor which is known to be cleaved, there are two AGK motifs towards the C-terminus of the protein. To determine if one, or both, of the AGK sites were recognized, time course pulse-chase radiolabeling of VV infected cells was carried out followed by immunoprecipitation with polyclonal α12L serum. Much to our surprise, we discovered that the 23 KDa A12L precursor was cleaved into a number of products including 15, 10.6 and 8 KDa species. Microsequence analysis of the products demonstrated that the three products arose by cleavage at one, two or all three of the AGX motifs. Interestingly, even with prolonged chase periods the precursor could not be chased to the fully processed 8 kDa product. Rather, all three products appeared to be stable with [10.6 KDa]>[15 KDa]>[8 KDa]. Furthermore, all three A12L-derived products could be found in the virion, suggesting they may have distinct biological functions. Thus, these results have identified a new variant, AGK, of the AGX motif which is cleaved in vivo and provided the first example of a VV core protein which is subject to a three step maturation pathway.

Example 5

VV Core Protein Processing is a Morphogenic Cleavage Pathway

As an approach to test whether VV core protein proteolysis serves a formative or morphogenic function in the virus life cycle, a method of sucrose log gradient fractionation was developed which allowed the separation and purification of radiolabeled immature and mature VV particles. Depending on the time postinfection that the infected cells were harvested, four distinct peaks of acid-precipitable counts could be detected that displayed different rates of sedimentation. Using pulse-chase procedures, the peaks could be shown to have precursor-product relationships as slower sedimenting entities chased into faster sedimenting ones with time. The peaks were referred to as A, B, C, and V particles, with A being the initial precursor form found near the top of the gradient and V being the fastest sedimenting product. As the previrions mature, they move faster in the gradient and become resistant to treatment with DNase 1. The core protein composition of the A particles was predominately uncleaved precursors, with only trace amounts of the mature core proteins, 4a, 4b, 25K and 23K present. However, as the sedimentation rate of the particles increased, proteolytic maturation proceeded such that C particles were composed almost exclusively of mature core proteins. Together, these results indicate that several distinct and separable forms of VV previrions exist, that VV core protein precursors are associated with previrions prior to cleavage, and that maturation of the core proteins is coordinately linked to the conversion from noninfectious previrions to infectious viral particles. This provides strong support for the hypothesis that VV core protein precursor maturation serves a morphogenic function.

In another set of experiments designed to monitor the intracellular and intraviral localization of the VV core proteins during infection, a collection of monospecific polyclonal antisera were produced that recognized individual core protein precursors and/or their cleaved products. Use of these sera in indirect immunofluorescence analyses of VV-infected cells demonstrated that the VV core protein precursors were not distributed throughout the cytoplasm of infected cells. Rather, the core protein precursors were localized almost exclusively to the "virosomes or virus factories" where the progeny virions were being assembled. At late times during infection, punctate staining was also evident throughout the cytoplasm which we believed to be individual virus particles. This hypothesis was confirmed by immunoelectron microscopy. The IEM studies also demonstrated that VV core protein precursors were associated with immature VV virions and that as the virions progressed through the maturation cycle the newly-processed core proteins remained associated with the condensing core.

The results of the experiments reported above indicate that the precursor form of the VV core proteins is required for proper localization to the virosome and assembling previrion. This raises the question of what feature of the core protein precursors is responsible for this behavior, as not all proteins present in a VV-infected cell are packaged. One can propose that it is the overall structure of the core proteins, the protein partners with which they interact, or the presence of a specific targeting signal that provides this property.

At least in the case of P4b and P25K, one candidate for a potential targeting signal is the N-terminal leader peptide that is removed by proteolysis during viral assembly. To test this hypothesis, a mutant P25K gene was constructed in which the sequence encoding the leader (the 31 N-terminal amino acids) was deleted. The (Δ31)P25K protein was expressed in the context of a VV-infected cell via transient expression. This protein, which should be functionally equivalent to mature 25K core protein, was not packaged into virions.

To determine if the entire leader of the core protein precursor was required to provide this phenotype, a set of deletions in the 61 amino acid leader of the P4b protein were constructed. Deletion of 15, 30 or 44 amino acids had no effect on P4b processing, indicating that the essential information was proximal to the cleavage site. Proof that it was the sequence or structure of the leader which imparted this property was provided by fusing the N-terminal 30 amino acids of the viral thymidine kinase (TK), a soluble early protein, to the 25K protein in a manner which reconstituted the AGA site. This TK:25K fusion protein was neither packaged nor processed.

Interestingly, the leaders of the core proteins appeared to be functionally interchangeable as two swap mutants were generated by making P4b leader:25K and P25K leader:4b chimeras. In both cases, the proteins could be packaged and processed. This result argues against the overall tertiary structure of the core protein precursors being the primary localization determinant as the fusion proteins would surely have disrupted structural features. Taken together, these data suggest that the amino terminal peptides of the VV core proteins are to some extent interchangeable and that the residues immediately proximal to the AGA site appear to contribute most directly to the correct intracellular and intraviral localization.

Example 6

Characterization of the Cis Signals Responsible for P25K Cleavage

Based on precedents in the viral proteinase literature, we attempted a number of different approaches to developing an assay system to study the proteolytic processing of VV core proteins. These included: (i) in vitro cleavage assays mixing VV core protein precursors isolated from cells infected with cleavage-deficient temperature-sensitive VV mutants together with extracts from wild-type VV-infected or uninfected cells; (ii) mixing solubilized VV virions with VV core protein precursors made in vivo or in vitro; (iii) co-translation of core protein precursor mRNA with mixtures of cellular and/or viral mRNA in rabbit reticulocyte lysates, and (iv) transient expression assays using the hybrid T7/VV system (52) to express various reporter gene constructs containing putative VV core protein cleavage sites.

Without exception, no cleavage of the test substrate was observed with any of these systems. This led, in part, to our working hypothesis that proteolytic maturation of VV core proteins is contextual, linked directly to virion assembly. The predictions of this hypothesis are that for a VV protein to be cleaved at the AGX motif it must be synthesized late in infection, packaged into the assembling virion, and associated with the VV core. Any perturbation of the kinetics of synthesis, intracellular targeting or structure of a VV core protein precursor might be expected to abrogate processing.

Testing this hypothesis required the development of an assay with which to examine the cis and trans factors mediating the proteolytic maturation of the VV core protein precursors in vivo. To accomplish this goal, several difficulties had to be overcome. First, the genes encoding the VV core protein precursors were thought to be essential for virus replication. Conditional-lethal mutants were not available in these loci, nor were these loci amenable to direct inactivation by gene insertion techniques known in the art. Second, the VV core proteins are relatively insoluble and difficult to work with in vitro. Third, on the basis of our earlier experiments, it appeared that cleavage occurs only within the context of a maturing virion particle. Fourth, the VV core protein precursors are highly expressed at late times during infection, making detection of an exogenously added core protein precursor difficult.

To overcome these challenges, a trans-processing assay to follow VV core protein proteolytic maturation was developed by tagging the P25K VV core protein precursor at the C-terminus with an octapeptide epitope, FLAG (55). The L4R gene was chosen as the target for these studies because it is the smallest of the three major core protein precursor genes, thus facilitating genetic manipulations, and because the L4R gene product, the P25K protein, is relatively soluble and amenable to biochemical analyses.

Figure 9:
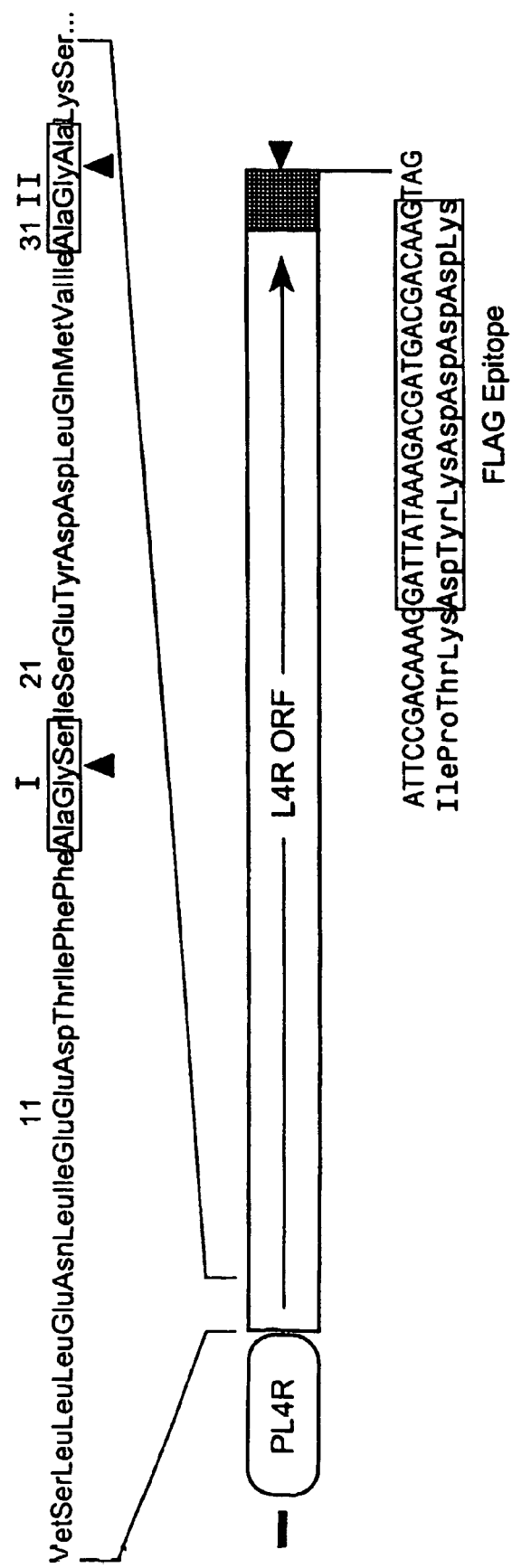

By using transient expression assays in cells co-infected with VV, the proteolysis of the P25K:FLAG fusion gene product could be monitored by immunoblotting and immunoprecipitation procedures using antisera specific for the FLAG epitope or the 25K protein. In vivo, the P25K:FLAG precursor was cleaved to smaller products and the precursor-product relationships were established by pulse-chase labeling protocols. The in vivo cleavage of the P25K:FLAG precursor was inhibited by rifampicin, implying that the reaction was using the same pathway as authentic VV core protein precursors. Moreover, the 25K:FLAG product was found in association with mature virions in accord with the hypothesis that cleavage occurs concomitantly with virion assembly. During these experiments, a potential cleavage intermediate (P25K') was identified in which processing was occurring at an AGS site located between residues 17–19 of the P25K leader (FIG. 9).

Site-directed mutagenic replacement of either or both of the primary AGA (positions 31–33) or the intermediate AGS (positions 17–19) sites within the P25K:FLAG precursor with the tripeptide IDI blocked cleavage at the mutated sites, indicating that both sites were used and recognized independently in vivo, and that bona fide proteolysis was occurring. The rate of P25K: FLAG precursor processing was about half that of the authentic P25K precursor. This observation was explained in part by using immunofluorescence to demonstrate that the P25K:FLAG protein was less efficiently targeted to the virosome. Since VV core protein processing appears to occur during virion assembly, it is likely that only the P25K:FLAG protein that is bound to the virosome enters the processing pathway.

The defect in targeting may be due to the altered structure of the P25K:FLAG precursor, or to the fusion gene being expressed from a plasmid as opposed to a genomic gene which is replicating within the virosome itself. In any case, these results provide biochemical and genetic evidence to establish the merits of the trans-processing assay and provide direct evidence that the AGX motif plays a direct role in cleavage site selection.

Although the central importance of the AGX motif in P25K processing is suggested by the failure of the IDI mutants to cleave, there must be additional determinants of cleavage site selection. Not all proteins containing an AGX motif are proteolytically cleaved. One such example is the AGN site of P4a which is not cut, despite the fact that two other downstream AGX sites in the same precursor are. Likewise, as discussed above, the VV DNA polymerase, palmitylated 37K envelope protein and the HR proteins all have AGA motifs which are not cleaved. Therefore, the AGX motif appears to be essential but not sufficient for defining a specific cleavage site. Additional substrate determinants within the precursors must contribute to cleavage site selection. As an approach to identify some of these other determinants, we have employed the trans-processing assay described above in concert with site-directed mutagenesis procedures. Specifically, using the P25K:FLAG gene as the template, substitution, insertion and deletion mutations were introduced in and around the AGA site. The phenotype of each individual mutant was analyzed by transient expression and immunoblotting procedures.

In all, more than 50 different P25K:FLAG mutants were constructed. The genotypes of the mutants were verified by sequencing and their phenotypes tested. The results obtained are summarized as follows, using the nomenclature of Schecter and Berger (56) in which the positions at the amino- and carboxyl proximal residues are indicated as P1, P2, etc., and P1', P2', etc., respectively. The residue occupancy of the P1' position was extremely permissive with only a proline substitution blocking cleavage. In contrast, the permissible occupancy of the P1 (serine or alanine) and P2 (cysteine, serine or asparagine) was extremely restricted. Analysis of P1/P2 double mutants supported this conclusion and suggested additional levels of combinatorial stringency. Insertion or deletion of sequences immediately adjacent (amino- or carboxyl terminal) to the AGA motif completely abrogated cleavage, suggesting the presence of additional structural elements. Mutation of the conserved proline or basic residues in these regions had no effect on cleavage, whereas it appeared that the presence of a hydrophobic residue in the P4 site was required.

Example 7

Candidates for vCPP—G1L and I7L a) G1L—As mentioned above, a large number of different approaches were attempted to reconstitute VV core protein proteolysis in vitro, and all were unsuccessful due to the contextual requirements of this reaction. Therefore, in order to identify the proteinase which is responsible for the cleavage of the VV core protein precursors it was necessary to implement an in vivo mapping procedure. To accomplish this goal, a transcriptionally-controlled trans-processing assay was developed.

Transcription of VV genes is tightly controlled by a regulatory cascade mechanism. All of the enzymes required for the synthesis and modification of early mRNA are packaged into the infectious virion. Following entry into the cell, early gene expression initiates viral DNA replication which leads to successive expression of intermediate and late viral genes. During a normal viral infection, it has been shown that newly replicated, naked, viral DNA serves as the template for the expression of the late transcription factor genes (AIL, A2L and G8R) as well as the late genes themselves. Transcription from an exogenously supplied late promoter in infected cells, whose DNA replication has been blocked by AraC, can be rescued by co-transfecting plasmid copies of the late transcription factor genes. This provided the basis for the development of the transcriptionally-controlled trans-processing assay using a plasmid copy of the P25K:FLAG ORF as the reporter gene.

Figure 10:
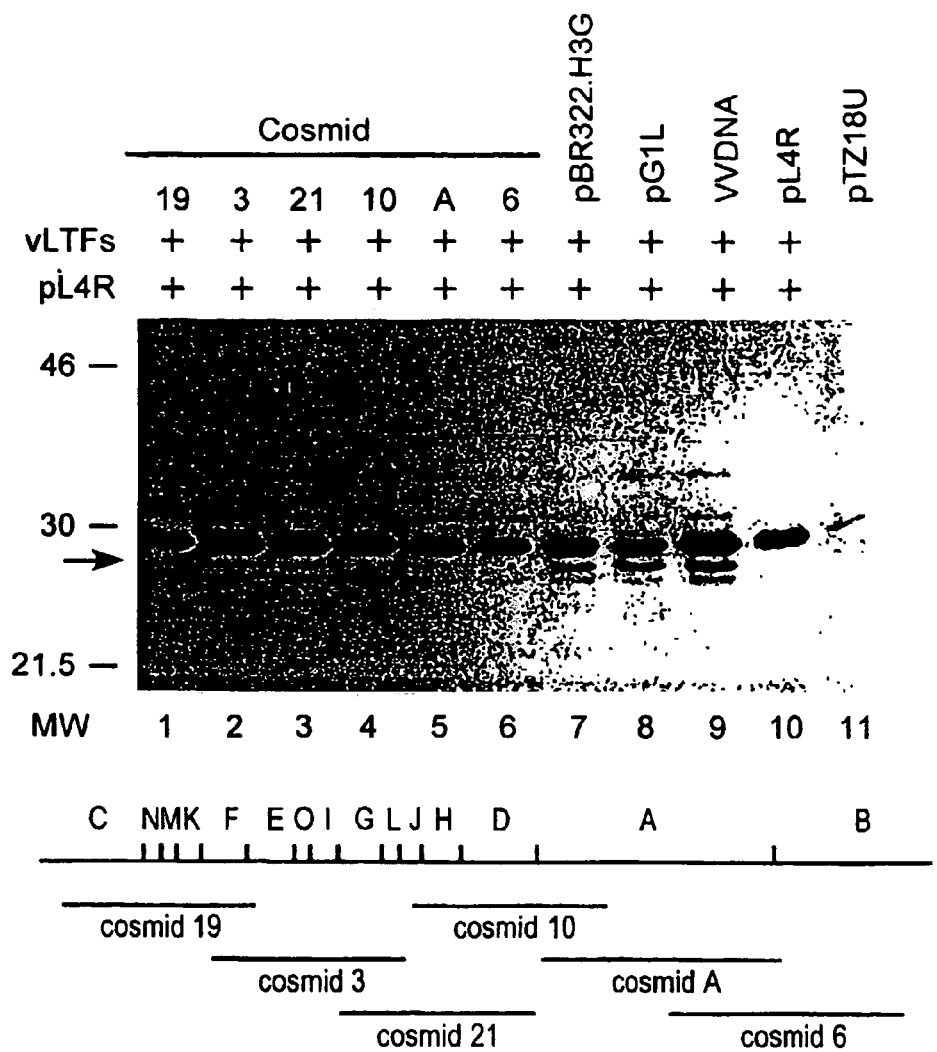

Cells were infected with VV in the presence of AraC to block late gene expression from the viral genome. Transfection of full-length VV DNA into AraC-treated VV-infected cells resulted in the expression and cleavage of VV core protein precursors, indicating that both processes (synthesis and processing) could occur under these conditions, and that the proteinase was likely the product of a VV late gene. In order to separate substrate expression and proteolysis, VV-infected cells treated with AraC were simultaneously transfected with plasmid copies of the following: (i) late gene transcription factors A1L, A2L and G8R; (ii) a test substrate; (iii) a potential source of proteinase. As the test substrate, the P25K:FLAG fusion gene was used. The initial source of proteinase was a set of 6 overlapping cosmid clones of the VV genome. Individually, cosmids 3 and 21 were able to rescue processing of the P25K:FLAG protein at the AGS site found at positions 17–19 within the N-terminal leader of the precursor. As these two cosmids overlapped in the HindIII G region, a cloned copy of the VV HindIII G fragment was tested and also found to direct cleavage of the substrate (FIG. 10).

Previously, we had used computer analyses to search the predicted amino acid sequences of all of the ORFs in the genomic sequence of VV(Copenhagen) for the presence of motifs that might suggest proteinase activity. The only "hit" we had was within the G1L ORF, which contained a HXXEH sequence motif, which is a direct inversion of the active site consensus sequence present in metalloproteinases such as thermolysin. Although the motif was backwards and there were no known examples of viral encoded metalloproteinases, we nevertheless cloned the G1L ORF, expressed it in vitro and tested it for the ability to cleave VV core protein precursors, without success.

A subclass of metalloproteinases, typified by the insulin-degrading enzymes, contain an inverted HXXEH motif (FIG. 11). Furthermore, we have come to appreciate the contextual nature of the VV core protein processing reaction. Thus, once we learned that the VV HindIII G fragment appeared to contain the gene for the core protein proteinase, we tested the cloned G1L gene in the transcriptionally-controlled trans-processing assay and discovered that it encoded the responsible proteinase. Molecular genetic experiments confirmed that the P25K:FLAG precursor was being cleaved within the AGS motif and that the conserved residues within the HXXEH motif of the G1L ORF were required for enzyme activity. These results strongly support the conclusion that the VV G1L protein is a metalloproteinase and implicate it as being responsible for the morphogenic proteolysis of VV core proteins.

b) I7L—Although there are several lines of evidence implicating G1L protein as the vCPP, we have recently identified a second candidate proteinase, the gene product of the I7L open reading frame. This protein was identified on the basis of homology to a ubiquitin-like proteinase in yeast. It is predicted to be a cysteine proteinase and two potential active sites are evident. Like G1L, I7L is highly conserved amongst the orthopoxviruses. I7L is predicted to encode a 47 KDa protein that is expressed at late times post-infection. Use of monospecific α-I7L antisera has demonstrated that the protein is associated with virus factories, immature viral particles and IMV, where it is exclusively located in the core.

A conditional lethal mutant in the I7L gene has been isolated. At the non-permissive temperature, the core protein precursors P4a, P4b and P25K are synthesized but not processed. Moreover, viral assembly is halted between immature viral particle formation and conversion to an infectious IMV particle. At the non-permissive temperature no infectious progeny are produced. All of these characteristics are those predicted for vCPP, thus providing further evidence for the importance of the I7L gene product.

As discussed above, based on the available evidence, amongst the 263 gene products encoded by VV, our two leading candidates for the vCPP are the proteins encoded by the G1L and I7L genes. Based on sequence information, G1L is predicted to be a metalloproteinase with an inverted HXXEH motif, whereas I7L is predicted to be a cysteine proteinase. As an initial approach to determining if either of these putative proteinases might be the vCPP, it was of interest to test a collection of class-specific proteinase inhibitors to determine their ability to inhibit VV replication in tissue culture cells.

To that end, $BSC_{40}$ tissue culture cells were infected with VV in the presence of various concentrations of proteinase inhibitors. Efforts were made to use concentrations of drugs which had minimal effects on the tissue culture cells, as judged by morphological appearance and thymidine incorporation. Inhibitors tested included: 1,10-phenanthroline, a metalloproteinase inhibitor, and it's non-chelating isomer, 1,7-phenanthroline; iodoacetamide, a cysteine inhibitor; and pepstatin A, an aspartic proteinase inhibitor. Unfortunately, we were unable to identify any serine proteinase inhibitors which were not acutely toxic to the host cell, perhaps not a surprising result given the ubiquity of this type of proteinase in mammalian cells. Interestingly, VV replication was completely blocked by 10 μM iodoacetamide or 1 μM 1,10-phenanthroline, whereas 1,7-phenanthroline or pepstatin A had no effect. These results are consistent with a metalloproteinase and a cysteine proteinase both playing an essential role in the viral replicative cycle. Thus both G1L and I7L remain as viable candidates for the vCPP.

In order to determine whether the G1L protein and/or the I7L protein is the vCPP, two complementary approaches are used: (1) phenotypic analysis of VV replication in the presence of proteinase inhibitors; and (2) construction of gene-specific conditional-lethal mutants.

Figure 12A:
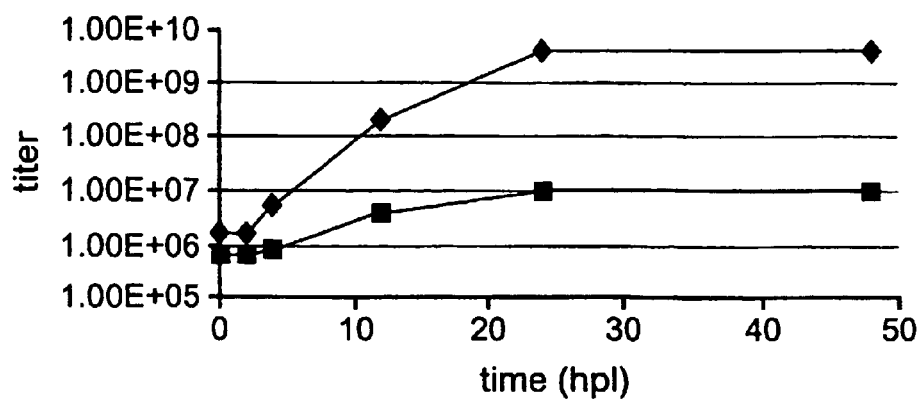
Figure 12B:
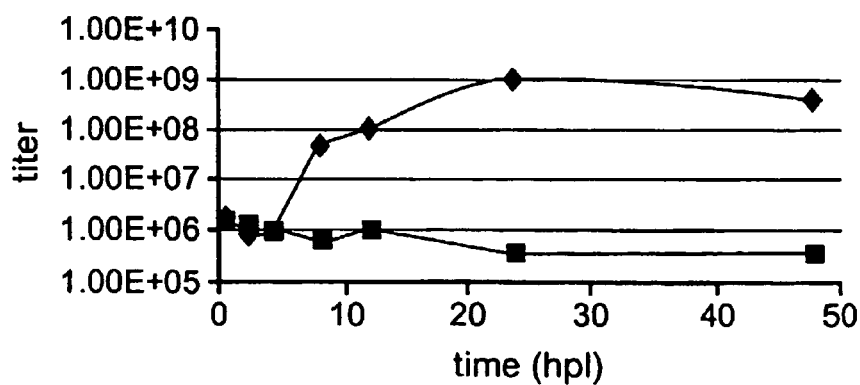

Phenotypic analysis takes advantage of the observation that iodoacetamide and 1,10-phenanthroline are both potent inhibitors of VV replication (FIG. 12), suggesting the obligatory requirement for a cysteine proteinase and a metalloproteinase, respectively, during the virus life cycle. Inhibition of this reaction is manifested by a phenotype in which viral early transcription and protein synthesis proceed normally, viral DNA synthesis and intermediate gene expression will occur, and viral late proteins will be made (including core protein precursors), followed by assembly of immature viral particles, while in the absence of cleavage, no mature infectious progeny are formed. Therefore, monolayers of $BSC_{40}$ cells infected with VV at a multiplicity of 10 plaque-forming units per cell in presence of 10 μM iodoacetamide or 1 μM 1,10-phenanthroline are subjected to several types of analyses:

a) Pulse labeling with $^{35}S$-methionine at 0, 2, 4, 6, 8 & 10 hours post-infection. Infected (±/− drug treatment) and control cell extracts are prepared at the indicated times and analyzed by SDS:PAGE and/or immunoblotting with a cocktail of anti-core protein antisera (4a, 4b, 25K). Analysis of the pattern of protein expression reveals if early proteins are expressed, if late proteins are expressed (and by inference if viral DNA has been synthesized).

b) DNA synthesis is directly measured by pulse-labeling with $^3H$-thymidine for 10 minutes at hourly intervals post infection. In the control situation, viral DNA synthesis is initiated at ~1.5 hours, peaks between 3–4 hours, and declines thereafter. Any deviation from the induction, peak or shut-off phases of the curve indicates inhibitor activity at a stage prior to core protein maturation.

c) Pulse-chase labeling is used to directly look at core protein processing. Infected cells (±/− drug) are labeled for 30 minutes with $^{35}S$-methionine at 4 hours post infection. Labeled medium is removed and replaced with medium containing 100× cold methionine and incubated for 1, 2, 3 and 4 hours post labeling prior to harvesting. Cell extracts are prepared at the indicated times and analyzed by SDS:PAGE and/or immunoblotting with a cocktail of anti-core protein antisera (4a, 4b, 25K). Analysis of the pattern of core protein expression directly indicates the presence or absence of vCPP activity d) Infectious progeny production is monitored by plaque assay. Both inhibitors prevent virus growth.

Figure 13A:
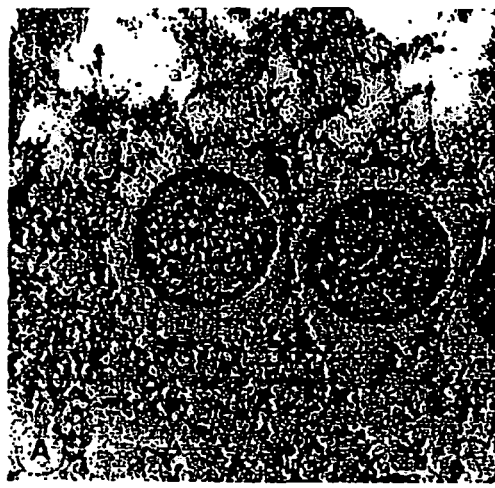
Figure 13B:
Figure 14:
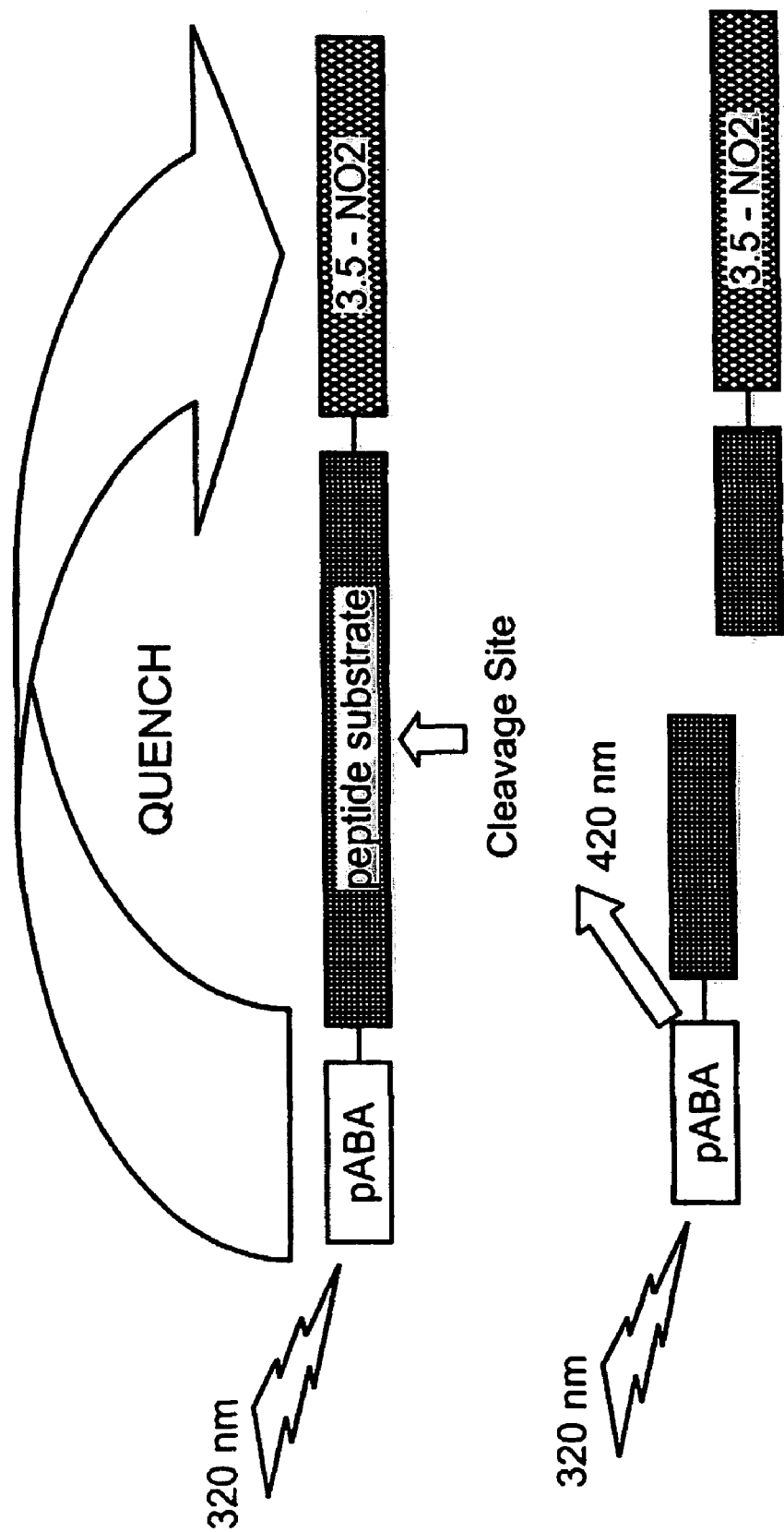
Figure 15:
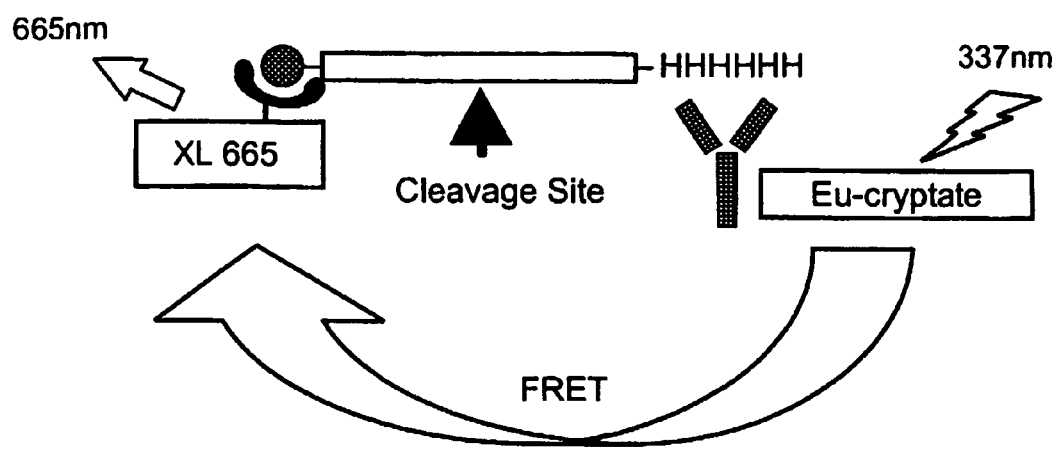

As the results of the above analyses are consistent with vCPP inhibition, infected cells (±/− drug) are prepared for transmission electron microscopy at 8 hours post infection. They are thin sectioned, stained, visualized by TEM, and photographed. In the absence of core protein maturation, immature particles are accumulated with little or no condensation of the viral cores as in FIG. 13.

The results of these experiments confirm G1L and I7L as candidates for vCPP, but they do not directly identify either gene product as the proteinase. This is because a variety of drugs or mutations whose target is clearly not vCPP manifest their phenotype in a similar fashion as above. For example α-amanitin and rifampicin, which inhibit the N2L and D13 gene products respectively, both have an abortive-late phenotype. This is likely due to the contextual requirement for core protein proteolysis. Anything which interferes with the correct assembly of the immature virion, is likely to inhibit core protein maturation.

As a more direct approach to addressing whether the G1L protein or the I7L protein are the vCPP, conditional-lethal mutant techniques can be used. Recombinant DNA plasmids are constructed which individually contain the regions of the VV DNA (WR strain) that contain the G1L or I7L gene, complete with its native promoter and sufficient flanking regions to catalyze homologous recombination into the viral genome (>500 bp). These plasmids also contain a second gene cassette with xanthine-guanine phosphoribosyltransferase (gpt) under the control of an independent VV transcriptional element, the 7.5K promoter. Using PCR-mediated insertional mutagenesis procedures, the lac operator (lacO) is inserted between the promoter/transcriptional start sites and the open reading frames of the G1L and I7L genes.

The structural authenticity of these dual recombination plasmids is verified by restriction enzyme analysis, PCR amplification and DNA sequencing of junction regions. The recombination plasmids are then transfected into $BSC_{40}$ cells that have been previously infected with vLacI, a recombinant VV strain which constitutively expresses the lac repressor. Recombinant virus is selected using mycophenolic acid (MPA, to block de novo purine biosynthesis), hypoxanthine (to drive the salvage pathway) and isopropylthiogalactopyranoside (IPTG, to induce expression of target gene). The virus stocks are passed several times under these conditions, and then several more times in the absence of MPA, but in the presence of IPTG. Under these conditions the initial recombination event is a single crossover, but in the absence of MPA selection the gpt cassette loops itself out and the lacO/target gene (G1L or I7L) becomes stably integrated as a double reciprocal crossover, replacing the native gene. Under these conditions the expression of the G1L and/or I7L is under the control of the lac operon. The expression of the gene of interest can then be regulated by the presence or absence of IPTG in the growth medium This approach has previously been successfully used to elucidate the function of a number of late genes including F18R, D13L, G8R, L4R and A5L. Our laboratory has used this method to study the function of L1R, a late VV myristylprotein, during virion assembly and morphogenesis. In most cases, the repressed phenotype can be reversed by addition of the IPTG at designated times post-infection. Importantly, the final proof of the function of the encoded gene can be provided by marker rescue of virus replication with a cloned copy of the target gene, in the presence of IPTG.

These approaches identified G1L and I7L as candidates for the vCPP. It should be noted however, that identification of other essential VV proteinases is not without merit or importance. Based on the results with other viral systems one can anticipate, given the mutagenic capability of most viruses, broad deployment of a specific proteinase inhibitor against vCPP would eventually result in the emergence of drug-resistant mutants. Therefore, having additional proteinase targets of different classes that participate at different points of the viral life cycle will provide second level targets in the future, if needed.

Example 8

Validation of vCPP as an Antiviral Target

Confirmation that the VV gene identified above is directly responsible for vCPP activity, and validation of this gene product as an appropriate antiviral target, proceeds in two stages. Provisional validation is provided by phenotypic analysis of the conditional-lethal mutants. Conclusive validation of the G1L or I7L proteins as the vCPP requires expression and purification of the individual gene product and development of a suitable cleavage assay to demonstrate the expected enzymatic activity in vitro (see below).

Phenotypic validation of the G1L and I7L genes as the target for antiviral drug development includes the following experiments:

a) Kinetics of protein expression and intracellular localization. Using the monospecific antisera generated herein, extracts of VV-infected cells are analyzed at various times post-infection to determine when the G1L and/or I7L proteins are expressed. Similarly, pulse-chase protocols are employed to determine if the proteins are stable or labile. Intracellular localization is determined by immunofluorescence and immuno-electron microscopy. vCPP is a viral late protein that co-localizes with VV core protein precursors and is found in immature virions. Information about the location and relative stability of vCPP will be valuable during subsequent efforts to express and purify the enzyme.

b) Replication defects of vlacO/G1L and vlacO/I7L. $BSC_{40}$ cells are infected with the vlacO/G1L and vlacO/I7L recombinants in the presence and absence of IPTG. The infected cells are analyzed for the production of infectious virus, viral protein synthesis, viral DNA synthesis, state of virion assembly and core protein cleavage as described above. The gene encoding vCPP yields an abortive late phenotype in the absence of IPTG. Whether the defective phenotype can be reversed at various times post-infection can be assessed by the addition of IPTG. Based on the reversibility of rifampicin-mediated inhibition on viral assembly and core protein maturation, this provides a means for synchronizing in vivo vCPP analyses.

b) Marker rescue of vlacO/G1L and vlacO/I7L recombinants. To directly prove that the G1L or I7L gene products are responsible for the observed phenotype, the ability to rescue virus replication with the wild-type gene is tested. $BSC_{40}$ cells are infected with vlacO/G1L and vlacO/I7L in the absence of IPTG, then transfected with either control plasmids or plasmids containing the G1L or I7L genes abutted to their native promoters. Extracts of the transfected cells are then assayed for mature virions by infectious plaque assay in the presence of IPTG.

Together, the results of these experiments reveal that the G1L and I7L gene products have the expected attributes of vCPP, and that absence of either activity gives the expected abortive-late phenotype.

Example 9

Characterization of the Vaccinia Virus I7L Core Protein Proteinase

The gene product of the I7L open reading frame was originally identified as a putative proteinase due to its homology to a ubiquitin-like proteinase in yeast, and shown to be one of the proteinases responsible for cleavage of the Vaccinia virus core proteins. While there is a relatively large amount of information about the sequences and characteristics of the cleavage of the core proteins, very little is known about the enzyme that carries out these reactions. The focus of this experiment is to show that I7L is capable of cleaving each of the core proteins and that mutagenesis of either the putative catalytic triad of I7L or of the Ala-Gly-Xaa sites in the precursor proteins abolishes this activity.

Materials and Methods:

Cells and Viruses—BSC40 cells were grown in Eagle's minimal essential medium containing 5% fetal calf serum (FCS), 2 mM glutamine, and 15 (g/ml gentamicin sulfate. Purified ts16 Vaccinia virus was prepared as described above. *Escherichia coli* strains were grown in Luria-Bertani broth or on Luria-Bertani medium containing 1.5% agar and ampicillin at 50 (g/ml).

Plasmids and Site-directed mutagenesis—See Table 1 for a description of all plasmids, oligos, and strains used. The Vaccinia virus P4a and P4b genes were amplified from Western Reserve strain genomic DNA with the primers CB40, CB41 and CB42, CB43 respectively and cloned into pRB21with NcoI and NheI and PstI and HindIII flanking yielding pP4a and pP4b. Site directed mutagenesis of the P4a gene was performed using the QuikChange® site-directed mutagenesis kit (Stratagene, Cedar Creek, Tex.) following the manufacturer's indications and using primers CB46,CB47,CB48, and CB49 to mutate the AGS (aa#613–615) and AGT (aa# 696–698) sites respectively to IDI residues, using pP4a as template. The same method was used for site-directed mutagenesis of the P4b gene using primers CB44 and CB45 to mutate the AGA (aa# 60–62) to IDI, using pP4b as template. Site-directed mutagenesis of the I7L gene was performed using the same kit using primers CB62 through CB73, and plasmid pI7L as template to individually mutate residues W(aa#242), D(aa#248), D(aa#258), Q(aa#322),C(aa#328), and G(aa#329) to A.

TABLE 1

PLASMIDS AND OLIGOS USED (the oligonucleotides are disclosed as SEQ ID NOS 1-24, respectively in order of appearance)

| Plasmid or Oligo | Description | Source |
|---|---|---|
| Plasmids | | |
| pCR2.1 | $Km^r$, $Amp^r$ | Invitrogen |
| pRB21 | puc derived with F13L flanks, MCS downstream of synthetic early/late promoter | Blasco |
| pP4a | pRB21 plasmid with P4a inserted between Ncol & Nhel sites | This work |
| pP4aIDI613 | pP4a with AGS (aa# 613–615) altered to IDI | This work |
| pP4aIDI696 | pP4a with AGT (aa# 696–698) altered to IDI | This work |
| pP4b | pRB21 plasmid with P4b inserted between Pstl and HindIII sites | This work |
| pP4bIDI | pP4b with AGA (aa# 60–62) altered to IDI | This work |
| pP25K | pRB21 plasmid with P25K with a FLAG epitope on the C-terminus cloned into MCS | Byrd |
| pP25:IDI | p25K plasmid with AGS (aa# 17–19) mutated to IDI | Byrd |
| pP25K:RPD | p25K plasmid with AGA (aa# 31–33) mutated to RDP | Byrd |
| p17L | pRB21 plasmid with full length 17L | Byrd |
| pH241A | pl7L with H (aa# 241) mutated to alanine | Byrd |
| pW242A | pl7L with W (aa# 242) mutated to alanine | This work |
| pD248A | pl7L with D (aa# 248) mutated to alanine | This work |
| pD258A | pl7L with D (aa# 258) mutated to alanine | This work |
| pQ322A | pl7L with Q (aa# 322) mutated to alanine | This work |
| pC328A | pl7L with C (aa# 328) mutated to alanine | This work |

TABLE 1-continued

PLASMIDS AND OLIGOS USED (the oligonucleotides are disclosed as SEQ ID NOS 1-24, respectively in order of appearance)

| Plasmid or Oligo | Description | Source |
|---|---|---|
| pG329A | pl7L with G (aa# 329) mutated to alanine | This work |
| pl7L-T | pl7L truncated at aa# 228 to remove N-terminal region of protein | This work |
| Oligonucleotides | | |
| CB40 | 5'-CTAGCTAGCATGATGCCTATTAAGTCAATAGTTACTCTTG-3' | This work |
| CB41 | 5'-CATGCCATGGCTACTTGTCGTCATCGTCTTTATAATCTTCAT CATCAAAAGAG-3' | This work |
| CB42 | 5'-AAACTGCAGATGGAAGCCGTGGTCAATAGCGATG-3' | This work |
| CB43 | 5'-CCCAAGCTTCTACTTGTCGTCATCGTCTTTATAATCAAATAGT TCTGTAATATGTCTAGC-3' | This work |
| CB44 | 5'-GATGACTTTATATCCATAGACATCAGAAATCAACGTACC-3' | This work |
| CB45 | 5'-GGTACGTTGATTTCTGATGTCTATGGATATAAAGTCATC-3' | This work |
| CB46 | 5'-CCTAGATATTTCTATATAGACATTCCCGAAGGAGAGGAA-3' | This work |
| CB47 | 5'-TTCCTCTCCTTCGGGAATGTCTATATAGAAATATCTAGG-3' | This work |
| CB48 | 5'-AGGATTATTACAATTATTGATATCTGTACCGTATCCATA-3' | This work |
| CB49 | 5'-TATGGATACGGTACAGATATCAATATTTGTAATAATCCT-3' | This work |
| CB39 | 5'-AAACTGCAGATGCATCATCATCATCATCATACCTCTAGATTT GTAATG-3' | This work |
| CB52 | 5'-CCCAAGCTTCTACTTGTCGTCATCGTCTTTATAATCTTCATCG TCGTCTAC-3' | This work |
| CB62 | 5'-TGTTATTTGTCTCATGCGAAATGTGTAATTTAT-3' | This work |
| CB63 | 5'-ATAAATTACACATTTCGCATGAGACAAATAACA-3' | This work |
| CB64 | 5'-GGAAATGTGTAATTTATGCCAAAAAACAATGTTTAG-3' | This work |
| CB65 | 5'-CTAAACATTGTTTTTTGGCATAAATTACACATTTCC-3' | This work |
| CB66 | 5'-GTATCCTTTTATGCCTCCGGAGGCAAT-3' | This work |
| CB67 | 5'-ATTGCCTCCGGAGGCATAAAAGGATAC-3' | This work |
| CB68 | 5'-GTGGAAGTTAATGCGCTGTTGGAATCT-3' | This work |
| CB69 | 5'-AGATTCCAACAGCGCATTAACTTCCAC-3' | This work |
| CB70 | 5'-CTGTTGGAATCTGAAGCCGGGATGTTATTAGT-3' | This work |
| CB71 | 5'-ACTAATAACATCCCGGCTTCAGATTCCAACAG-3' | This work |
| CB72 | 5'-TTGGAATCTGAATGTGCAATGTTTATTAGTTTG-3' | This work |
| CB73 | 5'-CAAACTAATAAACATTGCACATTCAGATTCCAA-3' | This work |
| Cell line | | |
| BSC40 | African Green Monkey Kidney cells adapted to grow at 40° C. | |
| Virus | | |
| VV WR | Western reserve strain of *Vaccinia* virus | |
| ts16 | Temperature sensitive *Vaccinia* virus with a mutation in the I7L orf | |

TABLE 1-continued

PLASMIDS AND OLIGOS USED (the oligonucleotides are disclosed as SEQ ID NOS 1-24, respectively in order of appearance)

| Plasmid or Oligo | Description | Source |
|---|---|---|
| *E. coli* | | |
| INVαF' | F' endA1 recA1 hsdR17($r_k^-$, $m_k^+$) supE44 thi-1 gyrA96rel A1O80 lacZAM15 A(lacZYA-argF)U169 | Invitrogen |

Co-expression experiments—Confluent monolayers of BSC40 cells in 6-well plates were infected with ts16 VV at a multiplicity of infection of 5 plaque-forming units per cell and transfected with 10 μg of plasmid DNA using DMRIE-C (Invitrogen, Carlsbad, Calif.) following the manufacturer's indications. Cells were harvested at 24 h post-infection by pipetting up and down to lift the cells from the surface. The crude extract was centrifuged at 15000 rpm for 10 min, the supernatant aspirated off, and the pellet resuspended in 80 μl of 1×PBS. This was freeze-thawed three times and then centrifuged at 2500 rpm for 3 min to sediment cellular debris. The supernatant fraction was analyzed by Western blot.

Western Blot Analysis—10 μl of the whole cell extract obtained above were run on SDS-polyacrylamide gels and transferred to PVDF (Pall, AnnArbor, Mich.) membranes. The membranes were incubated with a 1:1000 dilution of anti-FLAG antisera (Stratagene, Cedar Creek, Tex.) and then with a 1:2000 dilution of goat anti-mouse AP antibodies (Bio-Rad, Hercules, Calif.). The proteins were detected using the AP development system (Bio-Rad, Hercules, Calif.) following the manufacturer's instructions.

Ts16 rescue experiments—Confluent monolayers of $BSC_{40}$ cells in 100 mm plates were infected with ts16 at a multiplicity of infection of 3 and transfected with either pI7L, pH241A, pW242A, pD248A, pD258A, pQ322A, pC328A, pG329A, or pI7L-T. For controls have cells infected with ts16 alone and cells infected with Western reserve Vaccinia virus. Incubate at 40° C. for 24 hours. Cells were harvested, centrifuged, the pellet resuspended in 1 mL of PBS, freeze-thawed 3 times and then tittered to determine rescue of virus replication.

Figure 16:
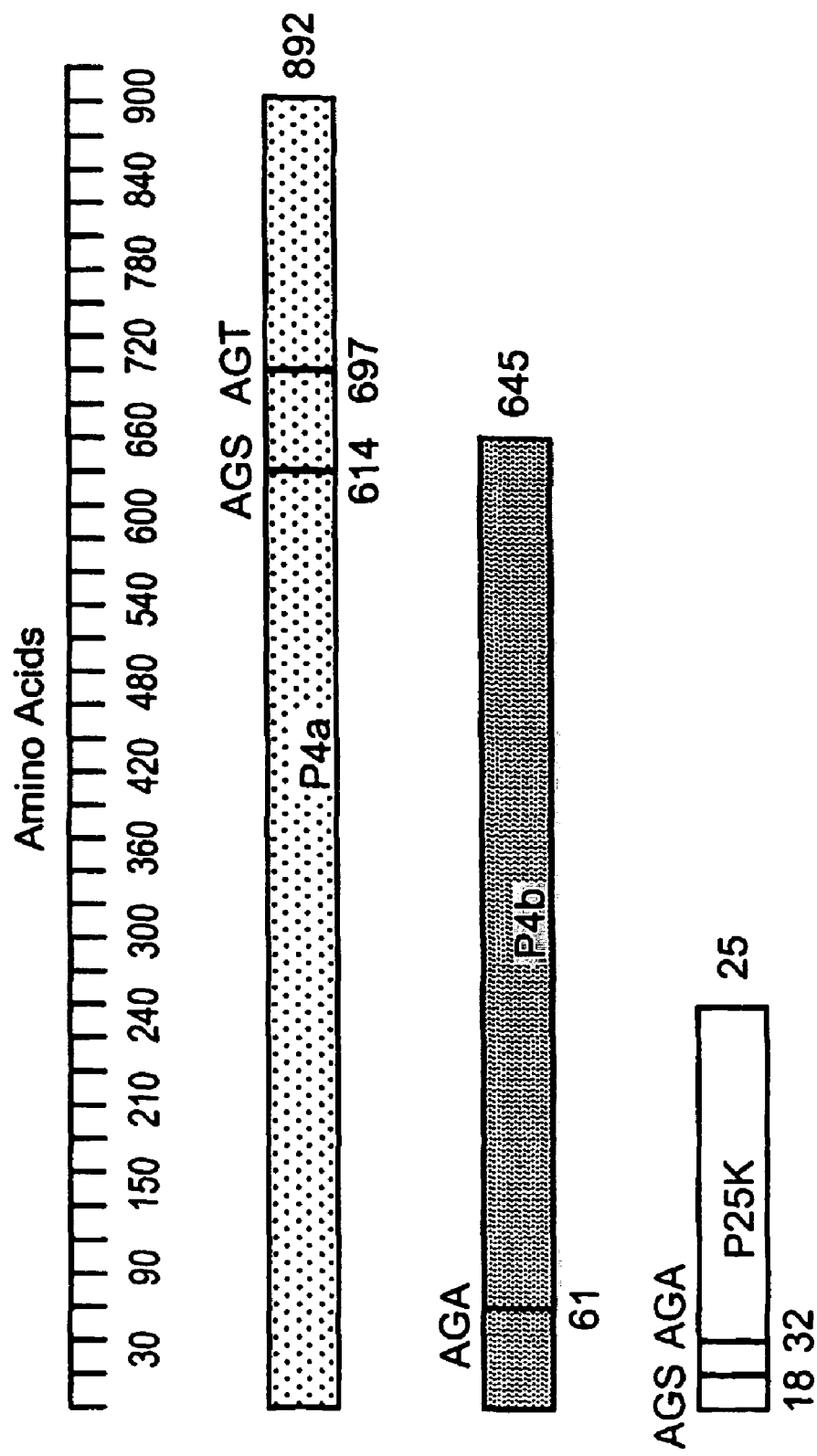

Results:

Core Protein Processing Activity of I7L—To determine whether I7L is responsible for cleavage of each of the core proteins, an in vivo trans processing assay was utilized where cells were infected with ts16 at the non-permissive temperature and co-transfected with plasmid born substrate and enzyme. Both the substrate proteins and I7L protease are constitutively expressed from a plasmid with a synthetic early-late promoter. Each core protein plasmid was designed with a FLAG epitope on the C-terminus for detection by Western blot. FIG. 16 is a map of the 3 major core proteins P4a, P4b, and P25 which are products of the A10L, A3L, and L4R open reading frames respectively, with the previously determined cleavage sites indicated on them. These cleavage sites have all been mapped to an AGX motif. P4a is the largest precursor protein with a molecular weight of 97 kDa and contains both an AGS and AGT cleavage site in the C-terminal region of the protein. P4b is a 67 kDa polyprotein with an N-terminal AGA site, and P25K is a 28 kDa polyprotein with both an AGS and AGA cleavage site in the N-terminal region of the protein.

Figure 17:
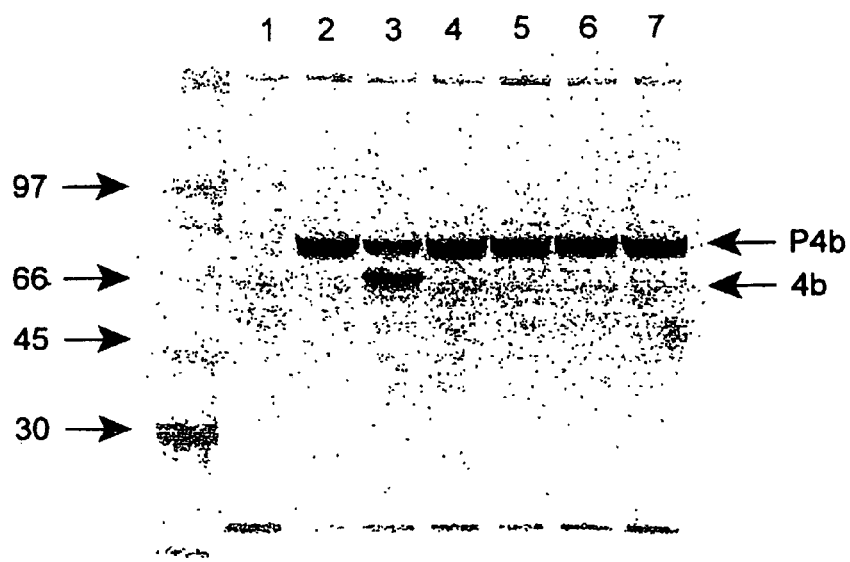

Cleavage of P25K by I7L has been previously demonstrated, but here we demonstrate that it is capable of directing cleavage of the other core protein precursors. FIG. 17 indicates that I7L cleaves P4b from its precursor form to the mature processed form (lane 3) but that when the histidine residue (a member of the putative catalytic triad) of I7L is mutated to an alanine, this cleavage is no longer observed (lane 4). Lanes 2 and 5 are controls showing P4b and P4bIDI expressed alone. Lane 1 shows uninfected cells indicating that there is no cross reactivity. When the AGA site of P4b is mutated to IDI residues, no cleavage by I7L is observed (lane 6). Lane 7 is a final control showing that with mutant P4b and mutant I7L no cleavage products are observed indicating that other proteases in the virus or cells are not causing the cleavage reactions.

Figure 18:
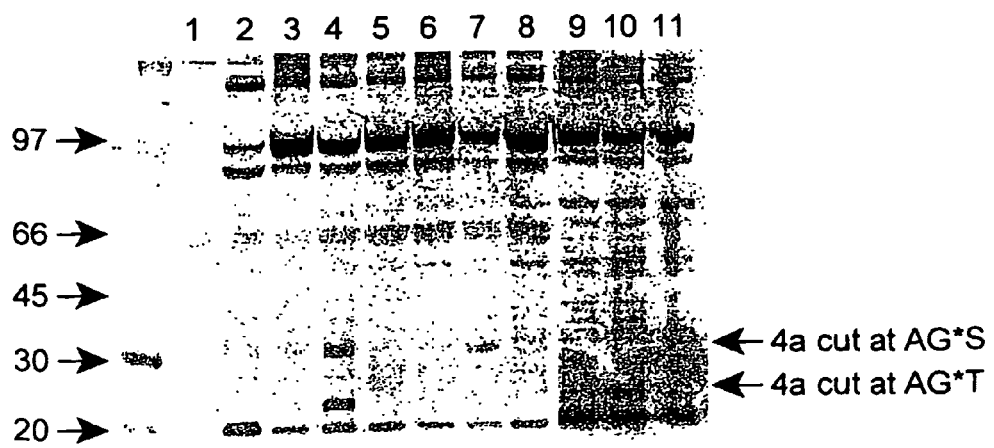

This experiment was repeated with the P4a polyprotein as shown in FIG. 18. When P4a is expressed alone (lane 3) it runs at its mature size of 97 kDa but when I7L is transfected in with P4a, two cleavage products are observed (lane 4) indicating that cleavage is occurring at both the AGS and AGT sites. Mutation of I7L abolishes this cleavage (lane 5). When the AGS site of P4a is mutated to an IDI and cotransfected with I7L, only one band at around 21 kDa is observed indicating cleavage at only the AGT site (lane 10). A similar result is obtained when the AGT site is mutated to an IDI (lane 7) where a faint band around 30 kDa is observed indicating cleavage is blocked at the IDI site but is still occurring to a small extent at the AGS site, indicating that the catalytic activity of I7L is necessary for cleavage to occur as well as the presence of the authentic cleavage sites.

Characterization of I7L—FIG. 19 shows a predicted hydrophobicity plot of the I7L protein using the Kyte-Doolittle program. The positions of the residues of the putative catalytic triad are indicated as well as the mutation that we've introduced to inactivate I7L. Also shown is the position of the ts16 mutation where a proline was altered to a leucine. Shown below the hydrophobicity profile are the Variola, Camelpox, and Monkeypox enzymes with positions of variance from VV I7L indicated with bars showing that these enzymes are highly homologous to VV I7L. In order to determine if the N-terminal domain of the protein is required for proteolytic processing, a truncated I7L was created with the size indicated relative to full length I7L. There is a conserved catalytic core domain between VV I7L, the ASFV protease, the adenovirus protease, and the *Saccharomyces cerevisiae* protease with several highly conserved amino acids. This is indicated in the bottom of FIG. 19 with arrows pointing at the conserved amino acids.

To determine which of these conserved amino acids is necessary for catalytic activity of I7L, site directed mutagenesis was performed on each in turn to mutate the residue of interest to an alanine. Transient expression assays were performed to test the activity of the mutant proteins on each of the core protein precursors. Western blots were performed using anti-I7L serum to test for expression of the enzyme as well as with FLAG monoclonal antisera to check for processing of the precursor proteins. Each of the mutant I7L enzymes was expressed equally well. FIG. 20 indicates that full length I7L is capable of cleaving each precursor protein but when either H# 241, W#242, D#248, Q#322, C#328, or G#329 is mutated to an alanine this cleavage is lost. The only mutant I7L that was still capable of cleavage was when D#258 was mutated to an alanine indicating that this might not be a member of the catalytic triad. Cotransfection with pD258A indicated that this protein was still capable of cleaving P25K and P4b, though cleavage of P4a was not indicated.

Marker Rescue—To demonstrate that I7L is capable of rescuing the growth and proteolytic processing activity of the ts16 virus, the virus was grown alone, in the presence of transfected full length I7L, and in the presence of transfected mutant I7L and truncated I7L at the non-permissive temperature, and then tittered to determine rescue. As shown in FIG. 21, full length I7L was capable of rescuing the growth of ts16 indicating that I7L is indeed the gene product that is mutated in ts16. Most of the mutant I7L enzymes and the truncated enzyme were incapable of rescuing growth of ts16, showing that the N-terminal portion of the enzyme is necessary. Both aspartic mutants recovered, but to a lesser extent than wild-type virus.

Discussion

The identity of the protein responsible to cleavage of the VV core protein precursors has been identified as the gene product of the I7L open reading frame. In this Example we further characterized the properties of this protein. The data reported here utilizing an in vivo trans processing assay with an epitope tagged substrate and plasmid borne enzyme has indicated that I7L is capable of driving the cleavage reaction and further verify that it is the viral core protein proteinase. Mutational analysis has shown that for this reaction to occur, catalytic activity of I7L is required and the authentic cleavage site has to be present in the substrate. This appears to be a global effect in that I7L is able to cut at the authentic AGA sites of P4b and P25K as well as the AGS and AGT sites within P4a, although it would appear that the cleavage of P4a and P4b is less efficient than that of P25K.

The I7L protein is characterized as a cysteine protease because mutation of the histidine, cysteine, and aspartic acid residues eliminates proteolytic activity. In addition, the other highly conserved residues in the catalytic core domain (W#242, Q#322, C#328, G#329) are all necessary for proteolysis to occur. The only residue that was not found to be essential for proteolysis was D#258.

Regardless of the type of proteolytic maturation utilized by the virus during maturation, it is essential that the activity of the viral proteinases be regulated to ensure efficient production of infectious progeny virions. In general, within biological systems, regulation of proteinases is achieved in several ways including differential compartmentalization of the enzymes and substrate, presence of specific inhibitors and/or activators, and the proteolytic activation of zymogens. Viruses have adopted similar strategies. For example in retroviruses, it has been proposed that the acidic extracellular environment triggers the morphogenic cleavage of structural proteins by displacing a portion of the gag-pol polyprotein which prevent the active site of the proteinase from interacting with its substrate while within the cell. In the case of adenoviruses, it appears that a disulfide-linked peptide produced from the pVI structural protein during the latter stages of replication as well as viral DNA is required for the activation of the viral proteinase and subsequent virus maturation.

While the invention has been described and illustrated herein by references to various specific material, procedures and examples, it is understood that the invention is not restricted to the particular material, combinations of material, and procedures selected for that purpose. Numerous variations of such details can be implied and will be appreciated by those skilled in the art.

What is claimed is:

1. An assay comprising the steps of:
   infecting cultured cells with vaccinia virus;
   co-transfecting the cells with one or more plasmids comprising DNA encoding the I7L protease enzyme and at least one substrate, such that both the substrate protein and enzyme are constitutively expressed; and
   measuring the amount of cleavage product of the I7L protease.

2. The assay of claim 1, wherein the cultured cells are infected with temperature-sensitive vaccinia virus at a non-permissive temperature.

3. The assay of claim 1, wherein the cultured cells are infected with wild-type vaccinia virus at a permissive temperature.

4. The assay of claim 1, wherein the substrate protein and enzyme are expressed from a synthetic early-late promoter.

5. The assay of claim 1, wherein the substrate protein is a core protein.

6. The assay of claim 5, wherein each core protein comprises a tag on the C-terminus of the protein.

7. The assay of claim 6, wherein the tag is a FLAG epitope.

8. The assay of claim 1, wherein the substrate is P25K also known as L4R.

9. The assay of claim 1, wherein the substrate is P4a also known as A10L.

10. The assay of claim 1, wherein the substrate is P4b also known as A3L.

11. The assay of claim 1, wherein the substrate is AI7L.

12. The assay of claim 1, wherein the vaccinia virus has a ts mutation in the I7L gene.

13. The assay of claim 1, wherein the cultured cells are $BSC_{40}$ cells.

* * * * *

SEQUENCE LISTING

<160> NUMBER OF SEQ ID NOS: 63

<210> SEQ ID NO 1
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
ctagctagca tgatgcctat taagtcaata gttactcttg                              40

<210> SEQ ID NO 2
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
catgccatgg ctacttgtcg tcatcgtctt tataatcttc atcatcaaaa gag              53

```
<210> SEQ ID NO 3
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
aaactgcaga tggaagccgt ggtcaatagc gatg                          34

<210> SEQ ID NO 4
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
cccaagcttc tacttgtcgt catcgtcttt ataatcaaat agttctgtaa tatgtctagc    60

<210> SEQ ID NO 5
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
gatgacttta tatccataga catcagaaat caacgtacc                     39

<210> SEQ ID NO 6
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
ggtacgttga tttctgatgt ctatggatat aaagtcatc                     39

<210> SEQ ID NO 7
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
cctagatatt tctatataga cattcccgaa ggagaggaa                     39

<210> SEQ ID NO 8
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
ttcctctcct cgggaatgt ctatatagaa atatctagg                      39
```

<210> SEQ ID NO 9
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
aggattatta caattattga tatctgtacc gtatccata                              39

<210> SEQ ID NO 10
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
tatggatacg gtacagatat caatatttgt aataatcct                              39

<210> SEQ ID NO 11
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
aaactgcaga tgcatcatca tcatcatcat acctctagat ttgtaatg                   48

<210> SEQ ID NO 12
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
cccaagcttc tacttgtcgt catcgtcttt ataatcttca tcgtcgtcta c              51

<210> SEQ ID NO 13
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
tgttatttgt ctcatgcgaa atgtgtaatt tat                                    33

<210> SEQ ID NO 14
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
ataaattaca catttcgcat gagacaaata aca                                    33

<210> SEQ ID NO 15

```
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
ggaaatgtgt aatttatgcc aaaaaacaat gtttag                              36

<210> SEQ ID NO 16
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
ctaaacattg ttttttggca taaattacac atttcc                              36

<210> SEQ ID NO 17
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
gtatcctttt atgcctccgg aggcaat                                        27

<210> SEQ ID NO 18
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
attgcctccg gaggcataaa aggatac                                        27

<210> SEQ ID NO 19
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
gtggaagtta atgcgctgtt ggaatct                                        27

<210> SEQ ID NO 20
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
agattccaac agcgcattaa cttccac                                        27

<210> SEQ ID NO 21
<211> LENGTH: 32
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
ctgttggaat ctgaagccgg gatgttatta gt                                    32

<210> SEQ ID NO 22
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
actaataaac atcccggctt cagattccaa cag                                   33

<210> SEQ ID NO 23
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
ttggaatctg aatgtgcaat gtttattagt ttg                                   33

<210> SEQ ID NO 24
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
caaactaata aacattgcac attcagattc caa                                   33

<210> SEQ ID NO 25
<211> LENGTH: 24
<212> TYPE: PRT
<213> ORGANISM: Vaccinia virus

<400> SEQUENCE: 25

Gly Ser Ile Ser Glu Tyr Asp Asp Leu Glu Met Val Ile Ala Gly Ala
 1               5                  10                  15

Lys Ser Lys Phe Pro Arg Ser Met
            20

<210> SEQ ID NO 26
<211> LENGTH: 9
<212> TYPE: PRT
<213> ORGANISM: Vaccinia virus

<400> SEQUENCE: 26

Ala Lys Ser Lys Phe Pro Arg Ser Met
 1               5

<210> SEQ ID NO 27
<211> LENGTH: 24
<212> TYPE: PRT
<213> ORGANISM: Vaccinia virus
```

-continued

<400> SEQUENCE: 27

```
Asn Ser Leu Ser Glu Ile Val Asp Asp Asp Phe Ile Ser Ala Gly Ala
  1               5                  10                  15

Arg Asn Glu Arg Thr Lys Pro Lys
             20
```

<210> SEQ ID NO 28
<211> LENGTH: 9
<212> TYPE: PRT
<213> ORGANISM: Vaccinia virus
<220> FEATURE:
<221> NAME/KEY: MOD_RES
<222> LOCATION: (8)
<223> OTHER INFORMATION: Variable amino acid

<400> SEQUENCE: 28

```
Ala Arg Asn Glu Arg Thr Lys Xaa Lys
  1               5
```

<210> SEQ ID NO 29
<211> LENGTH: 21
<212> TYPE: PRT
<213> ORGANISM: Vaccinia virus

<400> SEQUENCE: 29

```
Asp Thr Ile Phe Phe Ala Gly Ser Ile Ser Glu Tyr Asp Asp Leu Gln
  1               5                  10                  15

Met Val Ile Ala Gly
             20
```

<210> SEQ ID NO 30
<211> LENGTH: 21
<212> TYPE: PRT
<213> ORGANISM: Vaccinia virus

<400> SEQUENCE: 30

```
Ala Lys Ser Lys Phe Pro Arg Ser Met Leu Ser Ile Phe Asn Ile Val
  1               5                  10                  15

Pro Arg Thr Met Ser
             20
```

<210> SEQ ID NO 31
<211> LENGTH: 21
<212> TYPE: PRT
<213> ORGANISM: Fowlpox virus

<400> SEQUENCE: 31

```
Gly Glu Lys Ala Leu Cys Ala Gln Val Thr Arg Asp Gln Leu Leu Glu
  1               5                  10                  15

Ile Ile Ala Ala Gly
             20
```

<210> SEQ ID NO 32
<211> LENGTH: 21
<212> TYPE: PRT
<213> ORGANISM: Fowlpox virus

<400> SEQUENCE: 32

```
Ala Arg Ser Lys Phe Pro Lys Ser Leu Leu Ser Met Tyr Arg Val Thr
  1               5                  10                  15

Pro Arg Val Met Thr
             20
```

<210> SEQ ID NO 33
<211> LENGTH: 21
<212> TYPE: PRT
<213> ORGANISM: Vaccinia virus

<400> SEQUENCE: 33

Leu Ser Cys Ser Val Cys Asn Ser Leu Ser Gln Ile Val Asp Asp Asp
 1               5                  10                  15

Phe Ile Ser Ala Gly
            20

<210> SEQ ID NO 34
<211> LENGTH: 21
<212> TYPE: PRT
<213> ORGANISM: Vaccinia virus

<400> SEQUENCE: 34

Ala Arg Asn Gln Arg Thr Lys Pro Lys Arg Ala Gly Asn Asn Gln Ser
 1               5                  10                  15

Gln Gln Pro Ile Lys
            20

<210> SEQ ID NO 35
<211> LENGTH: 21
<212> TYPE: PRT
<213> ORGANISM: Fowlpox virus

<400> SEQUENCE: 35

Asn Leu Cys Asn Val Cys Asp Val Leu Asn Lys Ile Thr Glu Glu Asp
 1               5                  10                  15

Val Ile Ser Ala Gly
            20

<210> SEQ ID NO 36
<211> LENGTH: 21
<212> TYPE: PRT
<213> ORGANISM: Fowlpox virus

<400> SEQUENCE: 36

Ala Lys Gln Gln Arg Pro Met Arg Leu Arg Ser Lys Pro Lys Pro Asp
 1               5                  10                  15

Ile Cys Lys Gly Val
            20

<210> SEQ ID NO 37
<211> LENGTH: 21
<212> TYPE: PRT
<213> ORGANISM: Vaccinia virus

<400> SEQUENCE: 37

Gly Asp Ala Ala Val Lys Gly Gly Asn Asn Asn Leu Asn Ser Gln Thr
 1               5                  10                  15

Asp Val Thr Ala Gly
            20

<210> SEQ ID NO 38
<211> LENGTH: 21
<212> TYPE: PRT
<213> ORGANISM: Vaccinia virus

<400> SEQUENCE: 38

```
Ala Cys Asp Thr Lys Ser Lys Ser Ser Lys Cys Ile Thr Cys Lys Pro
  1               5                  10                  15

Lys Ser Lys Ser Ser
             20

<210> SEQ ID NO 39
<211> LENGTH: 17
<212> TYPE: PRT
<213> ORGANISM: Vaccinia virus

<400> SEQUENCE: 39

Met Ser Tyr Leu Arg Arg Tyr Tyr Asn Met Leu Asp Asp Glu Ser Ala
  1               5                  10                  15

Gly

<210> SEQ ID NO 40
<211> LENGTH: 21
<212> TYPE: PRT
<213> ORGANISM: Vaccinia virus

<400> SEQUENCE: 40

Ala Gly Val Leu Asp Lys Asp Leu Phe Thr Glu Glu Gln Gln Gln Ser
  1               5                  10                  15

Phe Met Pro Lys Asp
             20

<210> SEQ ID NO 41
<211> LENGTH: 21
<212> TYPE: PRT
<213> ORGANISM: Vaccinia virus

<400> SEQUENCE: 41

Gly Glu Asp Ile Phe Cys Ala Met Pro Tyr Asn Ile Leu Asp Arg Ile
  1               5                  10                  15

Ile Thr Asn Ala Gly
             20

<210> SEQ ID NO 42
<211> LENGTH: 21
<212> TYPE: PRT
<213> ORGANISM: Vaccinia virus

<400> SEQUENCE: 42

Thr Cys Thr Val Ser Ile Gly Asp Met Leu Asp Asn Ile Thr Thr Gln
  1               5                  10                  15

Ser Asp Cys Asn Met
             20

<210> SEQ ID NO 43
<211> LENGTH: 21
<212> TYPE: PRT
<213> ORGANISM: Vaccinia virus

<400> SEQUENCE: 43

Phe Arg Asp Tyr Gln Ser Tyr Arg Gln Tyr Arg Asn Tyr Cys Pro Arg
  1               5                  10                  15

Tyr Phe Tyr Ala Gly
             20

<210> SEQ ID NO 44
<211> LENGTH: 21
<212> TYPE: PRT
```

<213> ORGANISM: Vaccinia virus

<400> SEQUENCE: 44

Ser Pro Glu Gly Glu Glu Thr Ile Ile Cys Asp Ser Glu Pro Ile Ser
1 5 10 15

Ile Leu Asp Arg Ile
20

<210> SEQ ID NO 45
<211> LENGTH: 35
<212> TYPE: PRT
<213> ORGANISM: Vaccinia virus

<400> SEQUENCE: 45

Met Ser Leu Leu Leu Glu Asn Leu Ile Glu Glu Asp Thr Ile Phe Phe
1 5 10 15

Ala Gly Ser Ile Ser Glu Tyr Asp Asp Leu Gln Met Val Ile Ala Gly
20 25 30

Ala Lys Ser
35

<210> SEQ ID NO 46
<211> LENGTH: 39
<212> TYPE: DNA
<213> ORGANISM: Artificial Sequence
<220> FEATURE:
<223> OTHER INFORMATION: Description of Artificial Sequence: Synthetic nucleotide construct
<220> FEATURE:
<221> NAME/KEY: CDS
<222> LOCATION: (1)..(36)

<400> SEQUENCE: 46 att ccg aca aag gat tat aaa gac gat gac gac aag tag 39
Ile Pro Thr Lys Asp Tyr Lys Asp Asp Asp Asp Lys
1 5 10

<210> SEQ ID NO 47
<211> LENGTH: 12
<212> TYPE: PRT
<213> ORGANISM: Artificial Sequence
<220> FEATURE:
<223> OTHER INFORMATION: Description of Artificial Sequence: Synthetic peptide construct

<400> SEQUENCE: 47

Ile Pro Thr Lys Asp Tyr Lys Asp Asp Asp Asp Lys
1 5 10

<210> SEQ ID NO 48
<211> LENGTH: 11
<212> TYPE: PRT
<213> ORGANISM: Vaccinia virus

<400> SEQUENCE: 48

Gly Ile Ala His Leu Leu Glu His Leu Leu Ile
1 5 10

<210> SEQ ID NO 49
<211> LENGTH: 11
<212> TYPE: PRT
<213> ORGANISM: Escherichia coli

<400> SEQUENCE: 49

Gly Leu Ala His Tyr Leu Glu His Met Leu Phe

<210> SEQ ID NO 50
<211> LENGTH: 11
<212> TYPE: PRT
<213> ORGANISM: Drosophila melanogaster

<400> SEQUENCE: 50

Gly Leu Ala His Phe Cys Glu His Met Leu Phe
 1               5                  10

<210> SEQ ID NO 51
<211> LENGTH: 11
<212> TYPE: PRT
<213> ORGANISM: Homo sapiens

<400> SEQUENCE: 51

Gly Leu Ser His Phe Cys Glu His Met Leu Phe
 1               5                  10

<210> SEQ ID NO 52
<211> LENGTH: 11
<212> TYPE: PRT
<213> ORGANISM: Bacillus thermoproteolyticus

<400> SEQUENCE: 52

Val Val Ala His Glu Leu Thr His Ala Val Thr
 1               5                  10

<210> SEQ ID NO 53
<211> LENGTH: 11
<212> TYPE: PRT
<213> ORGANISM: Homo sapiens

<400> SEQUENCE: 53

Val Ile Ala His Glu Leu Ala His Gln Trp Phe
 1               5                  10

<210> SEQ ID NO 54
<211> LENGTH: 11
<212> TYPE: PRT
<213> ORGANISM: Homo sapiens

<400> SEQUENCE: 54

Val Ala Ala His Glu Leu Gly His Ser Leu Gly
 1               5                  10

<210> SEQ ID NO 55
<211> LENGTH: 22
<212> TYPE: PRT
<213> ORGANISM: Vaccinia virus

<400> SEQUENCE: 55

His Trp Lys Cys Val Ile Tyr Asp Lys Lys Gln Cys Leu Val Ser Phe
 1               5                  10                  15

Tyr Asp Ser Gly Gly Asn
            20

<210> SEQ ID NO 56
<211> LENGTH: 22
<212> TYPE: PRT
<213> ORGANISM: Vaccinia virus

<400> SEQUENCE: 56

```
Gly Cys Ile Asn Val Glu Val Asn Gln Leu Leu Glu Ser Glu Cys Gly
 1               5                  10                  15

Met Phe Ile Ser Leu Phe
            20

<210> SEQ ID NO 57
<211> LENGTH: 24
<212> TYPE: PRT
<213> ORGANISM: African swine fever virus

<400> SEQUENCE: 57

His Trp Val Ala Ile Phe Val Asp Met Arg Gly Asp Cys Trp Ser Ile
 1               5                  10                  15

Glu Tyr Phe Asn Ser Ala Gly Asn
            20

<210> SEQ ID NO 58
<211> LENGTH: 22
<212> TYPE: PRT
<213> ORGANISM: African swine fever virus

<400> SEQUENCE: 58

Leu Ala Val Thr Asn Ile Arg His Gln Arg Ser Gln Thr Glu Cys Gly
 1               5                  10                  15

Pro Tyr Ser Leu Phe Tyr
            20

<210> SEQ ID NO 59
<211> LENGTH: 22
<212> TYPE: PRT
<213> ORGANISM: Homo sapiens

<400> SEQUENCE: 59

His Trp Met Ala Phe Ala Trp Asn Pro Arg Ser Lys Thr Cys Tyr Leu
 1               5                  10                  15

Phe Glu Pro Phe Gly Phe
            20

<210> SEQ ID NO 60
<211> LENGTH: 23
<212> TYPE: PRT
<213> ORGANISM: Homo sapiens

<400> SEQUENCE: 60

Leu Glu Lys Ser Thr Gln Ser Val Gln Gly Pro Asn Ser Ala Ala Cys
 1               5                  10                  15

Gly Leu Phe Cys Cys Met Phe
            20

<210> SEQ ID NO 61
<211> LENGTH: 22
<212> TYPE: PRT
<213> ORGANISM: Saccharomyces cerevisiae

<400> SEQUENCE: 61

His Trp Ala Leu Gly Ile Ile Asp Leu Lys Lys Thr Ile Gly Tyr
 1               5                  10                  15

Val Asp Ser Leu Ser Asn
            20

<210> SEQ ID NO 62
<211> LENGTH: 22
```

-continued

```
<212> TYPE: PRT
<213> ORGANISM: Saccharomyces cerevisiae

<400> SEQUENCE: 62

Leu Ile His Leu Asp Cys Pro Gln Gln Pro Asn Gly Tyr Asp Cys Gly
 1               5                  10                  15

Ile Tyr Val Cys Met Asn
            20

<210> SEQ ID NO 63
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 63

His His His His His His
 1               5
```